United States Patent
Svigals

(10) Patent No.: US 9,319,404 B2
(45) Date of Patent: *Apr. 19, 2016

(54) SECURITY FOR THE INTERNET OF THINGS

(71) Applicant: Jerome Svigals, Redwood City, CA (US)

(72) Inventor: Jerome Svigals, Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/711,619

(22) Filed: May 13, 2015

(65) Prior Publication Data

US 2015/0249663 A1 Sep. 3, 2015

Related U.S. Application Data

(63) Continuation-in-part of application No. PCT/US2014/038164, filed on May 15, 2014, which is a continuation-in-part of application No. 14/053,373, filed on Oct. 14, 2013, now Pat. No. 8,997,188, which (Continued)

(51) Int. Cl.
*H04L 29/06* (2006.01)
*G06F 21/31* (2013.01)
(Continued)

(52) U.S. Cl.
CPC ............ *H04L 63/0853* (2013.01); *G06F 21/31* (2013.01); *G06F 21/44* (2013.01);
(Continued)

(58) Field of Classification Search
CPC . H04L 63/08; H04L 63/0853; H04L 63/0861; H04L 63/04; H04L 9/3228; H04L 9/3231; H04L 9/3234; G06F 21/305; G06F 21/31; G06F 21/44
See application file for complete search history.

(56) References Cited

U.S. PATENT DOCUMENTS 6,250,557 B1 6/2001 Forslund
6,394,341 B1 5/2002 Makipaa et al.
(Continued)

OTHER PUBLICATIONS

Parra et al., Flexible Smart Home Architecture using Device Profile for Web Services: a Peer-to-Peer Approach, International Journal of Smart Home, vol. 3, No. 2, Apr. 2009.*

(Continued)

*Primary Examiner* — Chau Le
(74) *Attorney, Agent, or Firm* — Edward J. Radlo; Radlo IP Law Group

(57) ABSTRACT

Apparati, methods, and computer-readable media for improving the security of communications networks. In one embodiment, an application control device (1102) controls another device (1109) from a remote location. The system comprises a remote device (1101) coupled to the device (1109) being controlled. The remote device (1101) has an action portion (1103) and a security portion (1104). The security portion (1104) contains a unique security portion identifier (1142). Remotely situated from the remote device (1101), the application control device (1102) comprises a rolling transaction code generator (1120) adapted to assign a unique rolling transaction code to each occurrence for which the application control device (1102) wishes to control the action portion (1103) of the remote device (1101). Another embodiment is a system for enabling two or more devices (1401, 1402, 1403) to communicate with each other over a network (1450) without human intervention. The system comprises at least one sending device (1401) adapted to send messages (1460) over the network (1450) to at least one receiving device (1402). Each sending device (1401) is coupled to the network (1450) via a sending intelligent chip (1411). Each receiving device (1402) is coupled to the network (1450) via a receiving intelligent chip (1421). Sending intelligent chip (1411) appends an identifier (1417) to each message (1460) emanating from its associated sending device (1401). The identifier (1417) comprises a fixed portion (1415, 1416) uniquely identifying the associated sending device (1401), and a variable portion (1414). Receiving intelligent chip (1421) comprises a module (1423) for approving the sent messages (1460), by validating both the fixed and variable portions of the identifier (1417).

10 Claims, 21 Drawing Sheets

Related U.S. Application Data is a continuation-in-part of application No. 13/895,155, filed on May 15, 2013, now Pat. No. 8,806,603, which is a continuation-in-part of application No. 13/444,551, filed on Apr. 11, 2012, now Pat. No. 8,453,223, which is a continuation-in-part of application No. PCT/US2013/036035, filed on Apr. 10, 2013, and application No. 13/444,551, Apr. 11, 2012.

(60) Provisional application No. 61/688,465, filed on May 16, 2012, provisional application No. 61/742,712, filed on Aug. 17, 2012, provisional application No. 61/795,190, filed on Oct. 12, 2012, provisional application No. 61/626,231, filed on Sep. 23, 2011.

(51) Int. Cl.
  *G06F 21/44* (2013.01)
  *H04L 9/32* (2006.01)
  *H04W 12/08* (2009.01)

(52) U.S. Cl.
  CPC ........... *H04L 9/3228* (2013.01); *H04L 9/3231* (2013.01); *H04L 9/3234* (2013.01); *H04L 63/04* (2013.01); *H04L 63/08* (2013.01); *H04L 63/0861* (2013.01); *H04W 12/08* (2013.01)

(56) References Cited

U.S. PATENT DOCUMENTS

| | | | |
|---|---|---|---|
| 6,516,416 B2 | 2/2003 | Gregg et al. | |
| 7,494,055 B2 | 2/2009 | Fernandes et al. | |
| 7,590,710 B1 | 9/2009 | Kokal et al. | |
| 7,753,259 B1 | 7/2010 | Taylor et al. | |
| 7,849,501 B2 | 12/2010 | Vishik et al. | |
| 7,861,082 B2 | 12/2010 | Pinder et al. | |
| 7,877,493 B2 | 1/2011 | Quinlan | |
| 7,925,708 B2 | 4/2011 | Davis et al. | |
| 7,991,434 B2 | 8/2011 | Yen et al. | |
| 7,996,324 B2 | 8/2011 | Bishop et al. | |
| 8,275,364 B2 | 9/2012 | Hubinak et al. | |
| 8,346,672 B1 | 1/2013 | Weiner et al. | |
| 8,380,177 B2 | 2/2013 | Laracey | |
| 8,417,947 B2 | 4/2013 | Bauer et al. | |
| 8,423,457 B1 | 4/2013 | Schattauer et al. | |
| 8,423,466 B2 | 4/2013 | Lanc | |
| 8,423,476 B2 | 4/2013 | Bishop et al. | |
| 8,453,223 B2 | 5/2013 | Svigals et al. | |
| 8,806,603 B2 | 8/2014 | Svigals et al. | |
| 8,997,188 B2 | 3/2015 | Svigals et al. | |
| 9,009,807 B2 | 4/2015 | Svigals et al. | |
| 2002/0046189 A1 | 4/2002 | Morita et al. | |
| 2002/0181703 A1* | 12/2002 | Logan | G06Q 20/382 380/30 |
| 2003/0221100 A1 | 11/2003 | Russ et al. | |
| 2004/0186768 A1 | 9/2004 | Wakim et al. | |
| 2004/0203384 A1 | 10/2004 | Sugikawa et al. | |
| 2004/0225776 A1 | 11/2004 | DiRaimondo et al. | |
| 2004/0230812 A1 | 11/2004 | Muller et al. | |
| 2004/0236838 A1* | 11/2004 | Tout | G06F 21/554 709/207 |
| 2004/0237100 A1 | 11/2004 | Pinder et al. | |
| 2005/0006468 A1* | 1/2005 | Fandel | G06Q 20/20 235/383 |
| 2005/0035192 A1 | 2/2005 | Bonalle et al. | |
| 2005/0127164 A1* | 6/2005 | Wankmueller | G06Q 20/04 235/380 |
| 2005/0240778 A1 | 10/2005 | Saito | |
| 2006/0018317 A1* | 1/2006 | Jimmei | H04L 29/12292 370/389 |
| 2006/0031173 A1 | 2/2006 | Rajaram | |
| 2006/0085635 A1* | 4/2006 | Park | H04L 63/08 713/159 |
| 2006/0163344 A1 | 7/2006 | Nwosu | |
| 2006/0178986 A1 | 8/2006 | Giordano et al. | |
| 2006/0235761 A1 | 10/2006 | Johnson | |
| 2007/0047466 A1 | 3/2007 | Todokoro | |
| 2007/0104180 A1 | 5/2007 | Aizu et al. | |
| 2007/0167194 A1 | 7/2007 | Brown et al. | |
| 2007/0170243 A1 | 7/2007 | Desany et al. | |
| 2007/0198432 A1 | 8/2007 | Pitroda et al. | |
| 2007/0254683 A1* | 11/2007 | Jie | H04L 12/585 455/466 |
| 2007/0289003 A1 | 12/2007 | Hamid et al. | |
| 2008/0147872 A1* | 6/2008 | Regnier | H04L 67/02 709/230 |
| 2008/0181208 A1 | 7/2008 | Maes | |
| 2008/0223925 A1 | 9/2008 | Saito | |
| 2008/0282334 A1 | 11/2008 | Yves et al. | |
| 2008/0301809 A1 | 12/2008 | Choi | |
| 2008/0319907 A1 | 12/2008 | Russell et al. | |
| 2008/0320591 A1 | 12/2008 | Fenton et al. | |
| 2009/0104888 A1 | 4/2009 | Cox | |
| 2009/0132808 A1 | 5/2009 | Baentsch et al. | |
| 2009/0144203 A1 | 6/2009 | Hurry | |
| 2009/0235339 A1 | 9/2009 | Mennes et al. | |
| 2010/0071031 A1 | 3/2010 | Carter et al. | |
| 2010/0088752 A1* | 4/2010 | Nagulakonda | H04L 9/3226 726/6 |
| 2010/0114677 A1 | 5/2010 | Carlson et al. | |
| 2010/0281535 A1* | 11/2010 | Perry, Jr. | G06Q 10/107 726/22 |
| 2010/0333169 A1 | 12/2010 | Hopen et al. | |
| 2011/0125565 A1 | 5/2011 | MacIlwaine et al. | |
| 2011/0238994 A1 | 9/2011 | Baentsch et al. | |
| 2012/0028606 A1* | 2/2012 | Bobotek | H04L 51/12 455/411 |
| 2012/0066498 A1 | 3/2012 | Engert | |
| 2012/0240195 A1 | 9/2012 | Weiss | |
| 2012/0253974 A1 | 10/2012 | Haikonen et al. | |
| 2013/0046990 A1 | 2/2013 | Fahrny et al. | |
| 2013/0081122 A1 | 3/2013 | Svigals et al. | |
| 2013/0232584 A1 | 9/2013 | Baentsch et al. | |
| 2013/0290078 A1 | 10/2013 | Svigals et al. | |
| 2014/0068729 A1 | 3/2014 | Svigals et al. | |
| 2014/0089076 A1 | 3/2014 | Svigals et al. | |
| 2014/0090018 A1 | 3/2014 | Svigals et al. | |
| 2015/0200914 A1 | 7/2015 | Svigals | |
| 2015/0201332 A1 | 7/2015 | Svigals | |

OTHER PUBLICATIONS

Wahab et al., GSM Based Electrical Control System for Smart Home Application, Feb. 2010, Journal of Convergence Information Technology, vol. 5, No. 1.*

Han et al., Smart Home Energy Management System using IEEE 802.15.4 and ZigBee, Sep. 2010, IEEE Transactions on Consumer Electronics.*

Natarajan et al., Development of an Infrastructure for the Management of Smart Homes, 2002, Computer Science Technical Reports, Paper 1540.*

International Search Report (ISA/AU) issued Jun. 3, 2013, for International Patent Application PCT/US2013/036035 filed Apr. 10, 2013, 4 pages.

Written Opinion of the International Searching Authority (ISA/AU) issued Jun. 3, 2013, for International Patent Application PCT/US2013/036035 filed Apr. 10, 2013, 4 pages.

Shankland, S., "Using NFC, IBM brings dual-factor authentication to mobile", CNET News, http://news.cnet.com/8301-1-11386_3-57608119-76/using-nfc-ibm-brings-dual-factor-authentication-to-mobile/, downloaded Oct. 18, 2013, 3 pages.

"Mobile Protection Pack", downloaded from https://mobileprotectionpack.att.com/core/jebber/next/gen/index.html May 14, 2014, 3 pages, copyright 2013-2014 by Asurion Mobile Applications, LLC.

International Preliminary Report on Patentability, issued Oct. 14, 2014, for International patent Application PCT/US2013/036035 filed Apr. 10, 2013, 5 pages.

International Search Report and Written Opinion (ISA/US) issued jan. 14, 2015, for International Patent Application PCT/US2014/038164 filed May 15, 2014, 12 pages.

* cited by examiner

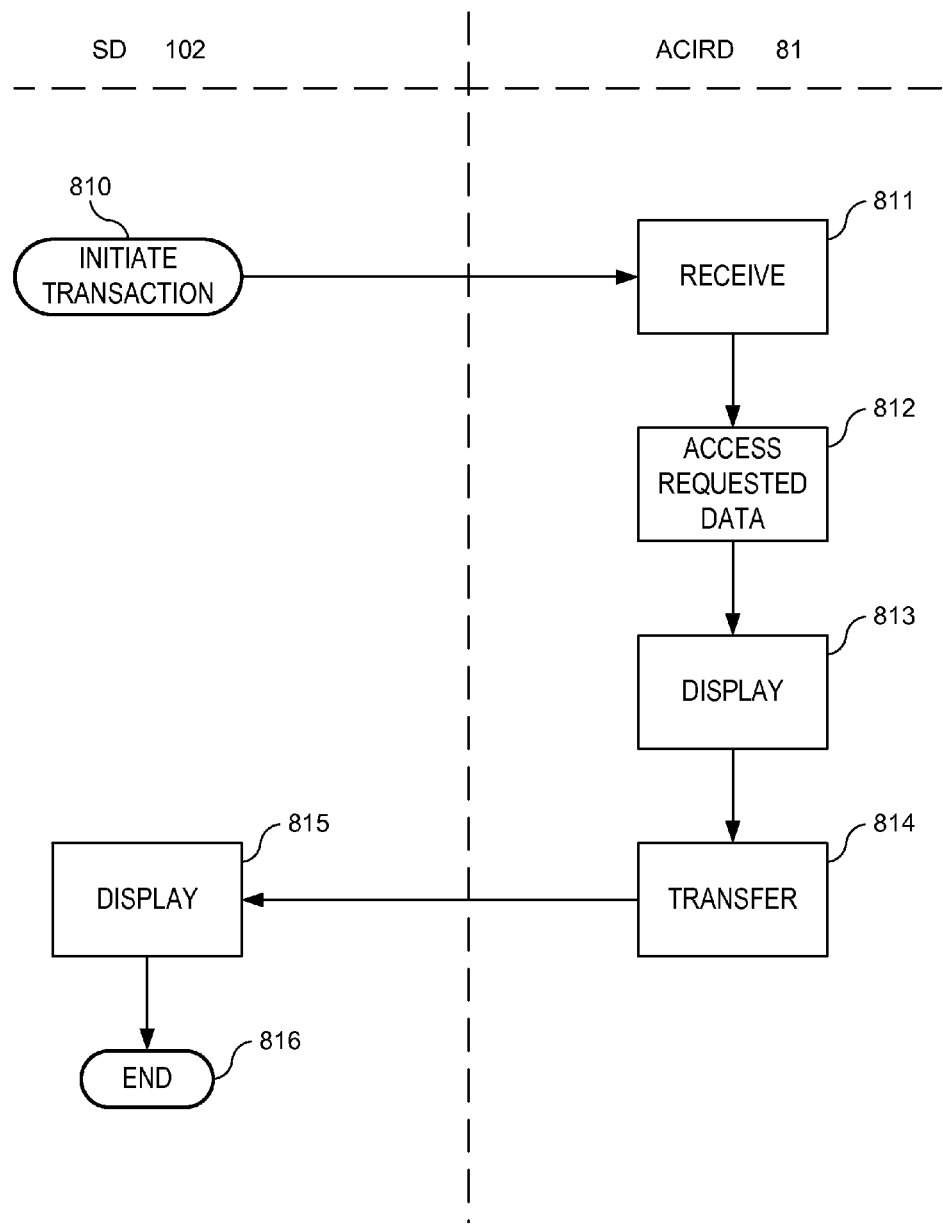
FIG. 8B1

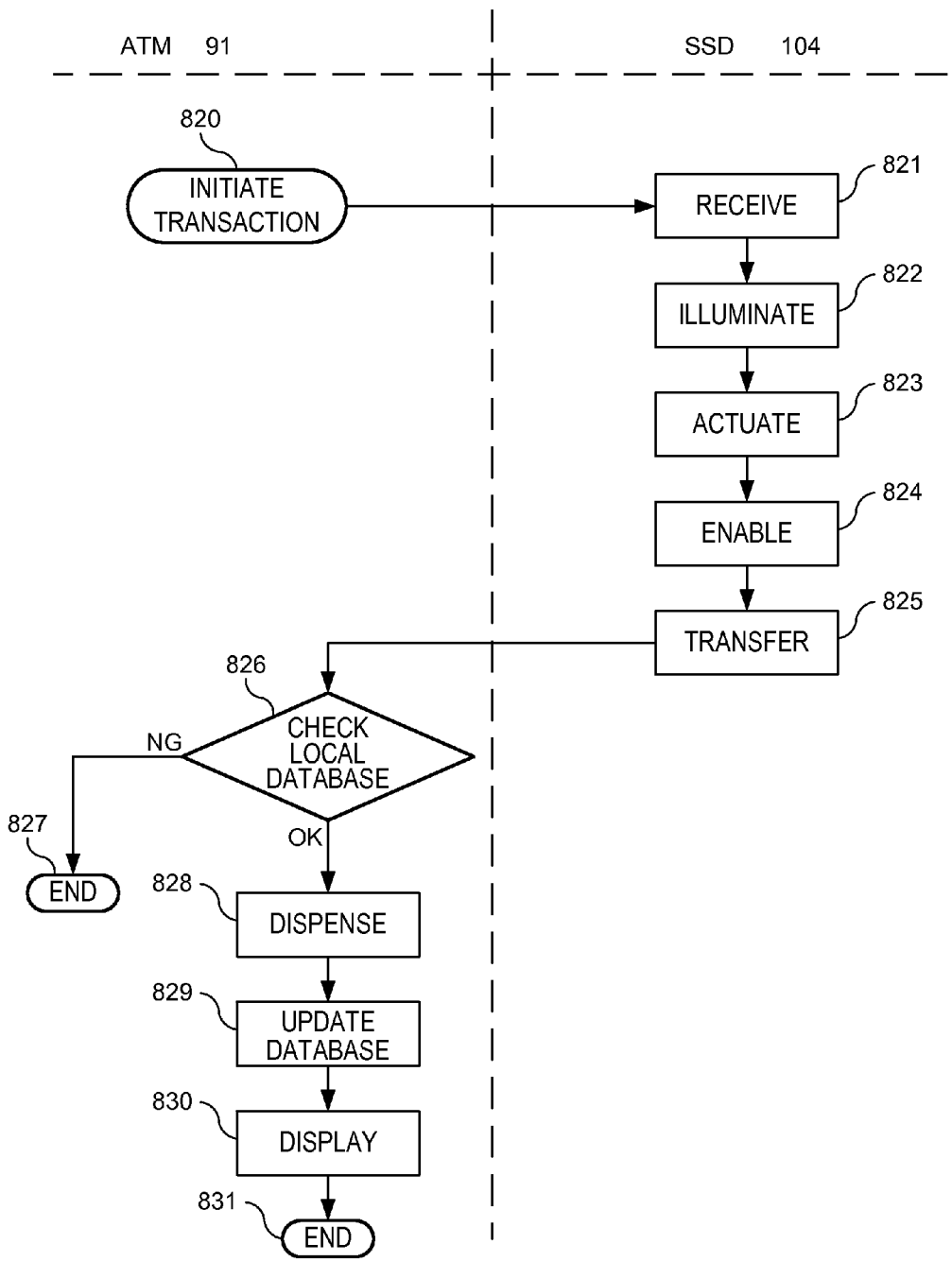
FIG. 8B2

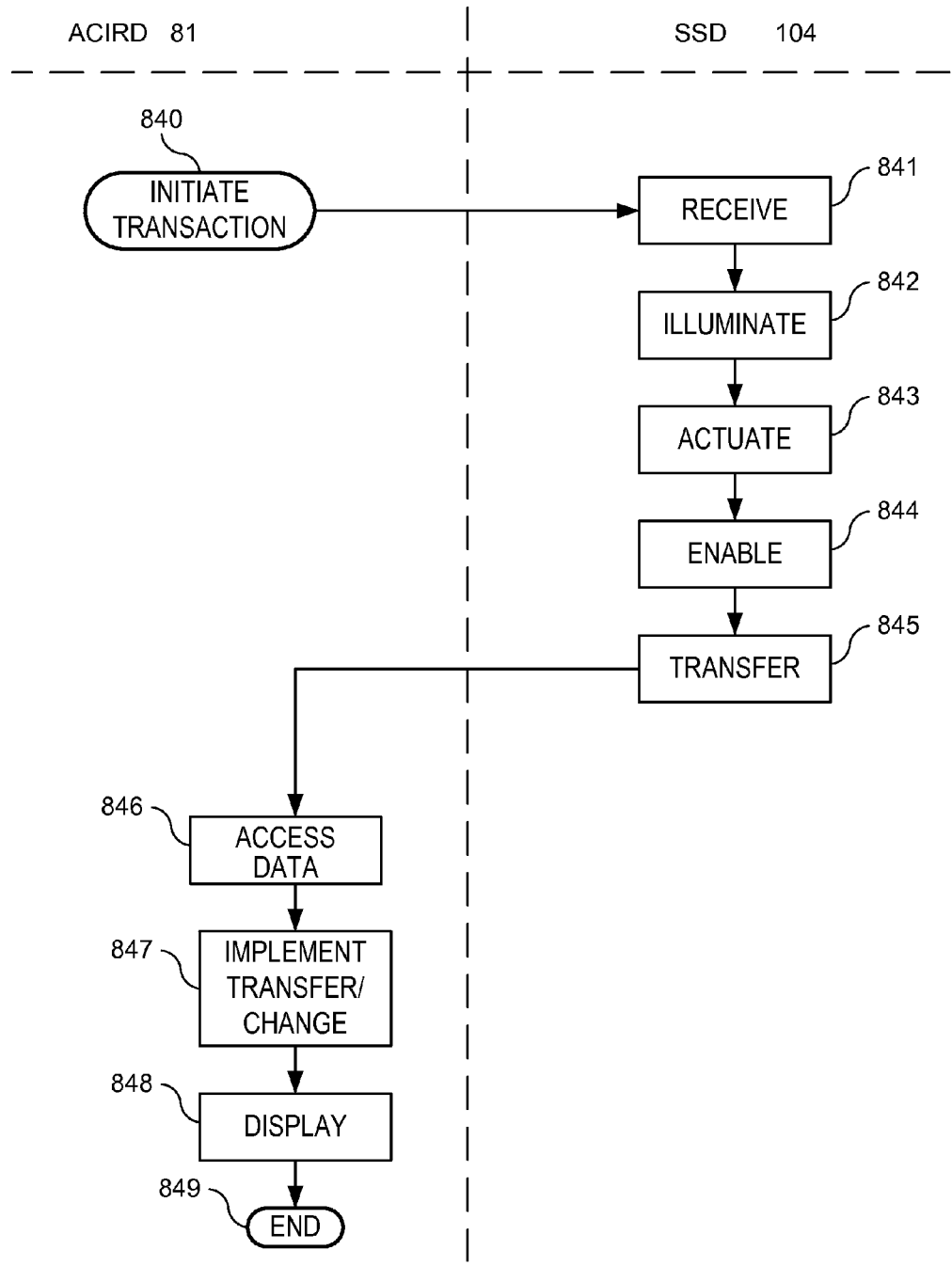
FIG. 8B3

SECURITY FOR THE INTERNET OF THINGS

CROSS-REFERENCES TO RELATED PATENT APPLICATIONS

This patent application is a continuation-in-part of co-pending PCT patent application PCT/US2014/038164 filed May 15, 2014, which is a continuation-in-part of U.S. patent application Ser. No. 14/053,373 filed Oct. 14, 2013, which issued as U.S. Pat. No. 8,997,188 on Mar. 31, 2015, which is a continuation-in-part of U.S. patent application Ser. No. 13/895,155 filed May 15, 2013, which issued as U.S. Pat. No. 8,806,603 on Aug. 12, 2014; U.S. patent application Ser. No. 13/895,155 is a continuation-in-part of U.S. patent application Ser. No. 13/444,551 filed Apr. 11, 2012, which issued as U.S. Pat. No. 8,453,223 on May 28, 2013, and U.S. patent application Ser. No. 13/895,155 also claims the priority benefit of U.S. provisional patent application 61/688,465 filed May 16, 2012, U.S. provisional patent application 61/742,712 filed Aug. 17, 2012, U.S. provisional patent application 61/795,190 filed Oct. 12, 2012, and is a continuation-in-part of PCT patent application PCT/US2013/036035 filed Apr. 10, 2013; U.S. patent application Ser. No. 13/444,551 in turn claims the priority benefit of U.S. provisional patent application 61/626,231 filed Sep. 23, 2011; all nine of these previous patent applications are hereby incorporated by reference in their entireties into the present patent application.

FIELD OF THE INVENTION

This invention relates to secure data transactions involving smart devices, communicating between and among themselves without human intervention. Very high levels of security are achieved without the use of encryption, PINs, or passwords.

BACKGROUND ART

The following background information may present examples of specific aspects of the prior art (e.g., approaches, facts, or common wisdom) that, while expected to be helpful to further educate the reader as to additional aspects of the prior art, is not to be construed as limiting the present invention, or any embodiments thereof, to anything stated or implied.

By way of educational background, some aspects of the prior art generally useful to be aware of are that techniques built into smart devices to provide security may include, for example, a biometric sensor built into a smart card; a smart device application program can encrypt the message content from the smart device to its controlling institution; and certain applications can be accessed by PINs (Personal Identification Numbers).

Another aspect of the prior art generally useful to be aware of is that some prior art may use key ring devices for assorted security or operational requirements, for example, a key ring device that computes a onetime password synchronized with a central site computer, and a key ring device used to convert wireless transmission to a second type of signal.

Mobile communication devices increasingly are used for performing operations associated with privileged access, such as financial transfers of funds. A lost, stolen, and/or compromised unsecured mobile communication device may result in significant harm to users and/or institutions. If the device is lost or stolen, the security device may be successfully manipulated by a thief, the communications may be overheard by unwanted people, and fraudulent downloads may be made.

In view of the foregoing, it is clear that these traditional techniques are not perfect and leave room for more optimal approaches.

DISCLOSURE OF INVENTION

The present invention comprises apparati, methods, and computer-readable media for improving the security of communications networks.

In one embodiment, an application control device (1102) controls another device (1109) from a remote location. The system comprises a remote device (1101) coupled to the device (1109) being controlled. The remote device (1101) has an action portion (1103) and a security portion (1104). The security portion (1104) contains a unique security portion identifier (1142). Remotely situated from the remote device (1101), the application control device (1102) comprises a rolling transaction code generator (1120) adapted to assign a unique rolling transaction code to each occurrence for which the application control device (1102) wishes to control the action portion (1103) of the remote device (1101).

Another embodiment is a system for enabling two or more devices (1401, 1402, 1403) to communicate with each other over a network (1450) without human intervention. The system comprises at least one sending device (1401) adapted to send messages (1460) over the network (1450) to at least one receiving device (1402). Each sending device (1401) is coupled to the network (1450) via a sending intelligent chip (1411). Each receiving device (1402) is coupled to the network (1450) via a receiving intelligent chip (1421). Sending intelligent chip (1411) appends an identifier (1417) to each message (1460) emanating from its associated sending device (1401). The identifier (1417) comprises a fixed portion (1415, 1416) uniquely identifying the associated sending device (1401), and a variable portion (1414). Receiving intelligent chip (1421) comprises a module (1423) for approving the sent messages (1460), by validating both the fixed and variable portions of the identifier (1417).

BRIEF DESCRIPTION OF THE DRAWINGS

The present invention is illustrated by way of example, and not by way of limitation, in the accompanying drawings, in which like reference numerals refer to similar elements.

FIGS. 8A through 8D are block and flow diagrams illustrating the use of SSD 104 and an ACIRD (ACI Response Device) 81 in an Industrial Application.

DETAILED DESCRIPTION OF PREFERRED EMBODIMENTS

Figure 1:
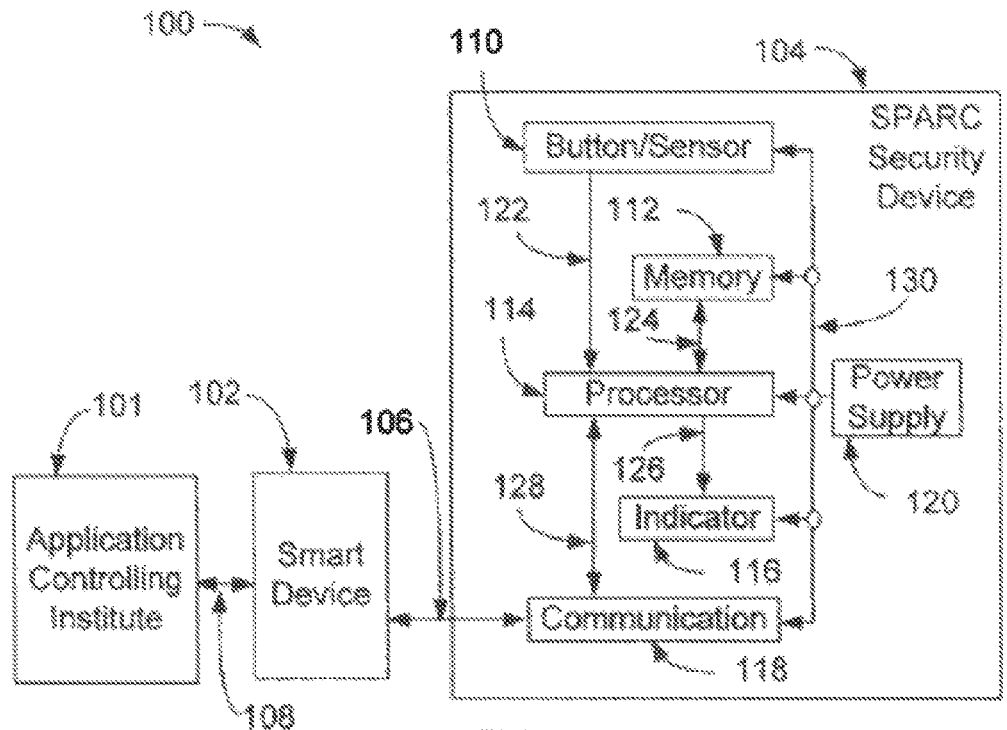
FIG. 1 is a block diagram of an example of a communication system, in accordance with an embodiment of the present invention.

Embodiments of the invention are discussed below with reference to the Figures. However, those skilled in the art will readily appreciate that the detailed description given herein with respect to these Figures is for explanatory purposes only, as the invention extends far beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments that are described and illustrated. There are numerous modifications and variations of the invention that are too numerous to be listed, but that fit within the scope of the invention.

It is to be further understood that the present invention is not limited to the particular methodology, compounds, materials, manufacturing techniques, uses, and applications described herein, as these may vary. It is also to be understood that the terminology used herein is for the purpose of describing particular embodiments only, and is not intended to limit the scope of the present invention.

Singular words should be read as plural and vice versa, and masculine as feminine and vice versa, where appropriate. Alternative embodiments do not necessarily imply that the two or more embodiments are mutually exclusive.

As used in this specification including claims, the singular forms "a," "an," and "the" include the plural reference, unless the context clearly indicates otherwise. Thus, for example, a reference to "an element" is a reference to one or more elements, and includes equivalents thereof known to those skilled in the art. Similarly, as another example, a reference to "a step" or "a means" is a reference to one or more steps or means, and may include sub-steps and subservient means. All conjunctions used are to be understood in the most inclusive sense possible. Thus, the word "or" should be understood as having the definition of a logical "or" rather than a logical "exclusive or", unless the context clearly indicates otherwise. Structures described herein are to be understood also to refer to functional equivalents of such structures. Language that may be construed to express approximation should be so understood, unless the context clearly indicates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures.

From reading the present disclosure, other variations and modifications will be apparent to persons skilled in the art. Such variations and modifications may involve equivalent and other features which are already known in the art, and which may be used instead of or in addition to features already described herein.

Although claims in this application have been formulated to particular combinations of features, it should be understood that the scope of the disclosure of the present invention also includes any novel feature or any novel combination of features disclosed herein, either explicitly or implicitly or any generalization thereof, whether or not it relates to the same embodiment as presently claimed in any claim, and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. Applicants hereby give notice that new claims may be formulated to such features and/or combinations of such features during the prosecution of the present application or of any further application derived therefrom.

References to "one embodiment," "an embodiment," "example embodiment," "various embodiments," etc., indicate that the embodiment(s) of the invention so described may include a particular feature, structure, or characteristic, but do not imply that every embodiment necessarily includes the particular feature, structure, or characteristic. Further, repeated use of the phrase "in one embodiment," or "in an exemplary embodiment," do not necessarily refer to the same embodiment, although they may.

As is well known to those skilled in the art, many careful considerations and compromises typically must be made when designing for the optimal manufacture of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, improved, and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not necessarily intended as synonyms for each other. Rather, in particular embodiments, "connected" may be used to indicate that two or more elements are in direct physical or electrical contact with each other. "Coupled" may also mean that two or more elements are in direct physical or electrical contact. However, "coupled" may mean that two or more elements are not in direct contact with each other, but yet still cooperate or interact with each other in some known or unknown manner.

A "computer" (or "Smart Unit") or "computing device" refers to one or more apparati and/or one or more systems that are capable of accepting a structured input, processing the structured input according to prescribed rules, and producing results of the processing as output. Examples of a "computer" include: a stationary and/or portable computer; a non-portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a Web appliance; a telecommunications device with Internet access (e.g., a Smartphone or other smart device); a hybrid combination of a computer and an interactive television; a tablet personal computer (PC); a personal digital assistant (PDA); a portable telephone; application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more programs, generate results, typically including input, output, storage, arithmetic, logic, and control units.

"Software" or "program" refers to prescribed rules to operate a computer. Examples of software include: code segments in one or more computer-readable languages; graphical and or/textual instructions; applets; pre-compiled code; interpreted code; compiled code; applications; and computer programs.

A "computer-readable medium" refers to any storage device used for storing data accessible by a computer. Examples of a computer-readable medium may include: a magnetic hard disk; a floppy disk; an optical disk, such as a CD-ROM or a DVD; a magnetic tape; a flash memory; a memory chip; and any other type of media that can store machine-readable instructions thereon.

A "non-transitory computer readable medium" includes, but is not limited to, a hard drive, compact disc, flash memory, volatile memory, random access memory, magnetic memory, optical memory, semiconductor based memory, phase change memory, optical memory, periodically refreshed memory, and the like; a "non-transitory computer readable medium" does not include a pure transitory signal per se.

A "computer system" refers to a system having one or more computers, where each computer may include a computer-readable medium embodying software to operate the computer or one or more of its components. Examples of a computer system include: a distributed computer system for processing information via computer systems linked by a network; two or more computer systems connected together via a network for transmitting and/or receiving information between or among the computer systems; a computer system including two or more processors within a single computer; and one or more apparati and/or one or more systems that accept data, process data in accordance with one or more stored software programs, and generate results, typically including input, output, storage, arithmetic, logic, and control units.

A "network" refers to a number of computers and associated devices that are connected by communication facilities. A network may involve permanent connections such as cables or temporary connections, e.g., those made through telephone or other communication links. A network may further include hard-wired connections (e.g., coaxial cable, twisted pair, optical fiber, waveguides, etc.) and/or wireless connections (e.g., radio frequency waveforms, free-space optical waveforms, acoustic waveforms, etc.). Examples of a network include: an internet, such as the Internet; an intranet; a local area network (LAN); a wide area network (WAN); and a combination of networks, such as an internet and an intranet.

Exemplary networks may operate with any of a number of protocols, such as Internet Protocol (IP), asynchronous transfer mode (ATM), synchronous optical network (SONET), user datagram protocol (UDP), IEEE 802.x, etc.

Embodiments of the present invention may include apparati for performing the operations disclosed herein. An apparatus may be specially constructed for the desired purposes, or it may comprise a general-purpose device selectively activated or reconfigured by a program stored in the device.

Embodiments of the invention may be implemented in one or a combination of hardware, firmware, and/or software. They may be implemented as instructions stored on a machine-readable medium, which may be read and executed by a computing (or smart) platform to perform the operations described herein.

In the following description and claims, the terms "computer program medium" and "computer readable medium" may be used to generally refer to one or more media such as, but not limited to, a removable storage drive, a hard disk installed in a hard disk drive, and the like. These computer program products may provide software to a computer system. Embodiments of the invention may be directed to such computer program products.

An algorithm (or application) is here, and generally, considered to be a self-consistent sequence of acts or operations leading to a desired result. These acts or operations include physical manipulations of physical quantities. Usually, though not necessarily, these quantities take the form of electrical or magnetic signals capable of being stored, transferred, combined, compared, and otherwise manipulated. It is convenient at times, principally for reasons of common usage, to refer to these signals as bits, values, elements, symbols, characters, terms, numbers, or the like. It should be understood, however, that all of these and similar terms are to be associated with the appropriate physical quantities, and are merely convenient labels applied to these quantities.

Unless specifically stated otherwise, and as may be apparent from the following description and claims, it should be appreciated that throughout the specification, descriptions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission, or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

Some embodiments of the present invention will be described which provide means and methods for a secure communication system. Secure communication systems include a Smart Device 102 with applications for communicating and interacting with a SPARC Security Device 104, a communication system that enables secure communications between a SPARC Security Device 104 and external entities to secure a communication system. Secure communication protocols use a transaction identifier for protecting transmitted and received return information.

The system will now be described in detail with reference to FIGS. 1 through 8.

FIG. 1 is a block diagram of an example of a communication system in accordance with an embodiment of the present invention.

Communication system 100 includes an Application Controlling Institution (ACI) 101, a Smart Device (SD) 102, and a SPARC (Smart Process for Applications and Remote Control) Security Device (SSD) 104. The SPARC Security device (SSD) 104 is provided by the Application Controlling Institution (ACI) 101 to a customer when the customer orders his or her first ACI controlled application. Alternatively, SSD 104 may be provided by a third party as an industry service. The SSD 104 is configured to match the communications protocol used by the customer's Smart Device (SD) 102. At the time of SSD 104 installation, the ACI 101 provides the initial data load of the SSD 104, including an assigned unique SSD number, current date, current time, and an initial transaction number (TN).

Application Controlling Institution (ACI) 101 communicates bi-directionally with Smart Device (SD) 102 via a communication channel 108. Smart Device (SD) 102 communicates bi-directionally with SPARC Security Device (SSD) 104 via a communication channel 106. Non-limiting examples for communication channels 106 and 108 include wireless, wired, and Universal Serial Bus (USB) channels. Channels 106 and/or 108 can comprise optical communications, e.g., in the form of a QR code. The optical communications do not have to be in a visible wavelength.

Application Controlling Institution (ACI) 101 receives, transmits, and processes information. As non-limiting examples, Application Controlling Institution (ACI) 101 may be a financial institution, an independent service, or an industry group such as MasterCard or VISA.

Smart Device (SD) 102 receives, transmits, and processes information. Examples of Smart Devices 102 include smart phones, cellular phones, tablet computers, tokens, automated teller machines (ATM), point of sale (POS) devices, transaction devices, networks such as those belonging to Visa and MasterCard, and PayPal.

SPARC Security Device 104 receives, transmits, and processes information. SSD 104 can have multiple controls for communicating with multiple ACI's 101. SPARC Security Device 104 communicates information to its human user via an indicator portion 116, and receives information from the user via a button and/or sensor portion 110. As a non-limiting example, sensor 110 may comprise a biometric sensor, such as a fingerprint reader.

SPARC Security Device 104 also includes a memory portion 112, a processor portion 114, a communication portion 118, and a power supply portion 120.

Processor portion 114 receives information from button/sensor portion 110 via a communication channel 122, and is adapted to signal agreement with the transaction. Processor portion 114 communicates bi-directionally with memory portion 112 via a communication channel 124. Indicator portion 116 receives information from processor portion 114 via a communication channel 126. Processor portion 114 communicates bi-directionally with communication portion 118 via a communication channel 128. Power supply portion 120 provides power to button/sensor portion 110, memory portion 112, processor portion 114, indicator portion 116, and communication portion 118, via a power supply bus 130.

Button/sensor portion 110 accepts receipt of digital information (e.g. "on"/"off") and/or analog sensor information from the user. Non-limiting examples for configuration of button/sensor portion 110 include a biometric sensor and an actuating button.

Memory portion 112 receives, stores, and retrieves information. Non-limiting examples of information stored include operational codes and data.

Processor portion 114 provides, receives, transmits, and processes information. Non-limiting examples of information received, transmitted, and processed include operational codes and data.

Indicator portion 116 provides capability for communicating information to the user. As a non-limiting example, indicator portion 116 may comprise a Light Emitting Diode (LED) or any other visual indicator, an audible alarm, and/or a vibrator.

Communication portion 118 provides capability for receiving and transmitting information to Smart Device 102. Non-limiting examples for communication provided via communication portion 118 include wired and wireless communication.

Power supply portion 120 provides power for powering the components of SSD 104. Non-limiting examples for power supply portion 120 include a rechargeable or other battery and an array of solar cells.

SPARC Security Device 104 constitutes a communication and processing device for creating a secure, identifiable transaction message to an institution 101 (e.g., bank or other financial institution). SPARC Security Device 104 can be configured for generating a one-time identifier ("SSD ID"). SPARC Security Device 104 can operate to initiate an action via another device, such as one or more Smart Devices 102. SPARC Security Device 104 can communicate and process information associated with a multiplicity of applications and/or a multiplicity of Smart Devices 102. For example, SPARC Security Device 104 can interact with a user's cellular phone device 102 and with the user's tabular computing device 102. SPARC Security Device 104 contains information for supporting operation of application programs associated with Smart Device 102.

Smart Device 102 and SPARC Security Device 104 can be configured to communicate only when geographically located within pre-established distance constraints, as specified for operation associated with communication channel 106. SPARC Security Device 104 may be an EMV (Eurocard/MasterCard/Visa) smart card or a NFC (Near Field Communications) smart card. An NFC smart card has a communication range of about 10 cm.

SPARC Security Device 104 contributes message content to messages assembled for communication from Smart Device 102 to Application Controlling Institution 101.

SPARC Security Device 104 and associated processes provide secure communications based upon the interaction of the two distinct devices, Smart Device 102 and SPARC Security Device 104, needed to complete a transaction with Application Controlling Institution 101.

The combination of Smart Device 102 with SPARC Security Device 104 provides a secure two-device method for preventing misuse or unauthorized use (e.g., fraudulent message replay, counterfeiting, etc.) of a lost or stolen Smart Device 102. Other devices aside from SPARC Security Device 104 are not capable of providing the required current value of the information to Smart Device 102 that SPARC Security Device 104 is capable of providing. Additional security is provided by the fact that Smart Device 102 is not capable of generating the ACI-required information associated with SPARC Security Device 104 to Application Controlling Institution 101 without first receiving it from the SPARC Security Device 104.

The two device interaction and processing associated with Smart Device 102 and SPARC Security Device 104 replace the identification portion (typically, the user's account number) of transaction information used in the prior art with information valid for just a single transaction. Said information is typically reconstituted to an unencrypted value, avoiding the need to provide the cumbersome key management that is associated with encryption. For the communication between Smart Device 102 and Application Controlling Institution 101, the user's real account number associated with a user account is replaced by the one-time identifier, which offers the following advantages:

1. The content of each substantive message becomes meaningless to those intercepting said message.
2. When a message is downloaded from ACI 101 to SD 102, SD 102 can use the SSD ID to screen out fraudulent messages.
3. Someone intercepting a message cannot use the information in the message to generate a fraudulent message, because the interceptor does not know the underlying algorithm that was used to generate the TN (transaction number).

In order to generate and store the one-time identifier (SSD ID), memory portion 112 includes at least two registers, containing: (1) a unique SSD 104 identifier; and (2) a one-time transaction number (TN). Optionally, memory 112 can also comprise the following registers associated with additional fields of the one-time identifier (SSD ID): (3) date, usually the current date; (4) time, usually the current time; (5) ACI 101 identifier, in case more than one ACI 101 is associated with the SSD 104; and (6) one or more additional fields designating subject matter, application, transaction type, etc. The combination of these fields becomes a temporary identifier ("SSD ID"), which replaces the user's true account number. Each ACI 101 maintains a corresponding database with a corresponding set of registers for each user account. Verification of the SSD ID is performed by ACI 101 checking for agreement between the components of the SSD ID of the incoming message and the components of the SSD ID stored within the ACI 101.

When there is an ACI 101 field in the SSD ID, an application in the SD 102 can tell the SSD 104 which ACI 101 to work with. Alternatively, the SSD 104 can itself determine which ACI 101 to work with, by consulting a pre-established table within the SSD 104. In this embodiment, SSD 104 can deal with multiple ACI's 101 directly, without having to designate a primary ACI 101. If there were no ACI 101 field in the SSD ID, one ACI 101 is designated as the primary ACI 101, and coordinates communications between or among the other ACI's 101.

Any and all of the SPARC Security Device 104 parameters can be made to be programmable. Such parameters can include the allowable response time before timing out, loss of an NFC signal, the range of allowable operation, etc.

An SSD 104 may be enabled to communicate using several different communications protocols, such as NFC, Bluetooth, and/or WiFi.

An ACI 101 can issue several cards to the same user. These cards can be debit cards, gift cards, loyalty cards, and/or prepaid cards. The SSD ID can include a function or card field (such as field (6) described above) to enable the ACI 101 to distinguish among the various card holdings for the specific transaction.

Assuming that ACI 101 successfully verifies the bona fides of the incoming message, the one-time transaction number (TN) is changed by the ACI 101. The one-time transaction number could be incremented by 1, but it is far preferable to change the one-time transaction number by a more complex incrementation algorithm. Said algorithm is securely pre-stored in both the ACI 101 and the SSD 104. Subsequent messages having an incorrect value for the one-time transaction number are rejected by ACI 101. This inhibits overheard transaction re-use and fraudulent message download. Upon receipt of a valid SSD ID that matches an SSD ID within its database, ACI 101 gains access to the associated true user account number. The ACI 101 database (which is indexed by the SSD number or one-time transaction number), enables ACI 101 to process the message using the true account number.

The one-time transaction number can comprise bits that represent other than numerical data, such as alphabetical or alphanumeric data. Thus, whenever the expression "TN" is used in this specification, it should be considered to mean "transaction identifier" in the more general sense. A given message can have a first one-time transaction identifier, and the corresponding response can have a different one-time transaction identifier. The transaction identifier serves to differentiate messages sent to and received from the ACI 101; and enables the detection of duplicate SSD 104 use, counterfeit messages, counterfeit SSD 104 use, and illegal use of lost or stolen Smart Devices 102. The number of digits comprising the transaction identifier can be expanded, when the transaction identifier is advanced, to reduce the possibility of successful attacks. A transaction identifier can be replaced by the ACI 101 to counteract ACI 101 database attacks, misuse, or theft.

Communication system 100 operates via interaction of Smart Device 102, SPARC Security Device 104, and the user. If Smart Device 102 and SPARC Security Device 104 are not both available to the user, the processing of and communication of information to Application Controlling Institution 101 is not performed. However, when just SPARC Security Device 104 is unavailable, the user can continue to use Smart Device 102 for other applications not associated with SPARC Security Device 104 (e.g., word processing, Internet browsing, etc.).

SPARC Security Device 104 supports a multiplicity of actuating devices 110. Non-limiting examples of actuating devices include manual, biometric (e.g., fingerprint), dual, and automatic. Furthermore, the actuating device 110 variations offer two or three factor security control, as desired by the user. Two factor authentication is an approach to authentication involving the presentation of two different kinds of evidence for verification. Two factor authentication is associated with something a user knows and something for which a user is in physical possession. Three factor authentication includes two factor authentication, with the addition of something uniquely related to the identity of a person (e.g., a fingerprint).

The interaction of SPARC Security Device 104 with each Smart Device 102 can be performed via the same communications protocol for all devices 102, or by more than one protocol.

Communication system 100 supports "bump" security applications. "Bump" comprises an application operating via a Smart Device 102 and by a matching algorithm operating via servers connected to SD 102 via communication channel 108.

SPARC Security Device 104 supports an arbitrarily large number of applications operating on a given Smart Device 102.

Applications associated with Smart Device 102 and/or SPARC Security Device 104 can detect an attempt to record information communicated between the devices 102, 104.

Application Controlling Institution 101 can modify, disable, remove, or destroy applications associated with Smart Device 102.

Smart Device 102 and SPARC Security Device 104 support message rejection by Application Controlling Institution 101, where appropriate. This support includes reprocessing and retransmitting the message, modification of an application program, and destroying a portion (or all) of an application program.

SPARC Security Device 104 supports maintenance of an audit trail for transactions initiated by SPARC Security Device 104 for communication by Smart Device 102 to Application Controlling Institution 101. As a non-limiting example, the audit trail can include the original SSD ID. The audit trail information can be used to replace the original account identifiers for information communicated to or from Application Controlling Institution 101 to one or more audit computing devices (not shown). Audit trail information is typically used for generation of messages to Application Controlling Institution 101, as the associated information is not current with respect to the current time and message count content.

Applications associated with SPARC Security Device 104 can be used for securing transaction messages communicated from Application Controlling Institution 101 to computing devices other than SD 102 and SSD 104. Such information transmitted by Application Controlling Institution 101 may be compared with information contained within SPARC Security Device 104.

Transmitted message content between and among the devices 101, 102, 104 can be verified for accuracy via parity checks. For example, Application Controlling Institution 101 may perform parity checks on received information. As a non-limiting example, parity checks can be performed via a Cyclic Redundancy Check (CRC).

Applications to be run on Smart Device 102 and SPARC Security Device 104 can be securely uploaded and updated via the communication processes associated with Smart Device 102 and SPARC Security Device 104.

SPARC Security Device 104 may continue to be used in the event of a lost or stolen Smart Device 102.

In some embodiments, the functionality of SPARC Security Device 104 is performed by a second Smart Device 102 device, with the second Smart Device 102 simulating the operation of a SPARC Security Device 104 device.

In some embodiments, Smart Device 102 is configured to refuse to perform a requested action prior to configuration for operation with SPARC Security Device 104. As a non-limiting example, when an unauthorized user attempts to perform unauthorized transactions via the Smart Device 102 (e.g., a financial fund transfer), the Smart Device 102 does not communicate with external entities until configuration and communication with SPARC Security Device 104 is performed. As a non-limiting example, unauthorized telephone toll charges may be prevented via this feature. Furthermore, this feature may be configured for functions associated with Smart Device 102 in order to support monitoring for security device surveillance. This feature enables a user to monitor and control operation of Smart Device 102.

ACI 101 (or a licensed third party device) assigns the associated unique SSD 104 unit identifier, and a pre-established initial transaction identifier for new application acceptance, to applications to be used on SD 102. The unique SSD 104 unit identifier and the initial transaction identifier are then communicated to SPARC Security Device 104 for confirmation. If confirmed, SPARC Security Device 104 signals the user, e.g., by illuminating indicator portion 116 in a pre-established manner, and requests confirming actuation by the user via button/sensor portion 110. If not confirmed by the user's actuating button/sensor 110, SPARC Security Device 104 generates an alert, e.g., a flash or other signal repeatedly illuminating indicator 116.

Smart Device 102 can use an access application confirmation process for preventing unauthorized access to the applications stored in SD 102. This access application confirmation process can use a biometric actuator to confirm the user's privilege to access SD 102.

For a lost or stolen Smart Device 102 containing a valid SSD unit number, SSD 102 is not able to create an acceptable message to ACI 101, because SD 102 does not have the one-time Transaction Number.

When an incorrect SSD unit number is presented to ACI 101, an ACI 101 application detects the incorrect SSD unit number and rejects the attempted transaction.

Normally, the same human user controls both the SSD 104 and the SD 102.

Downloading a message from ACI 101 to SSD 104 requires the correct SSD 104 number, plus the correct one-time transaction number.

An attempt to use multiple SPARC Security Devices 104 with a single Smart Device results in an unusable signal received by Smart Device 102, which results in rejection (by ACI 101 and SD 102) of all messages generated by all the SPARC Security Devices 104. It would be cumbersome to have a separate SSD 104 for each application.

Figure 2:
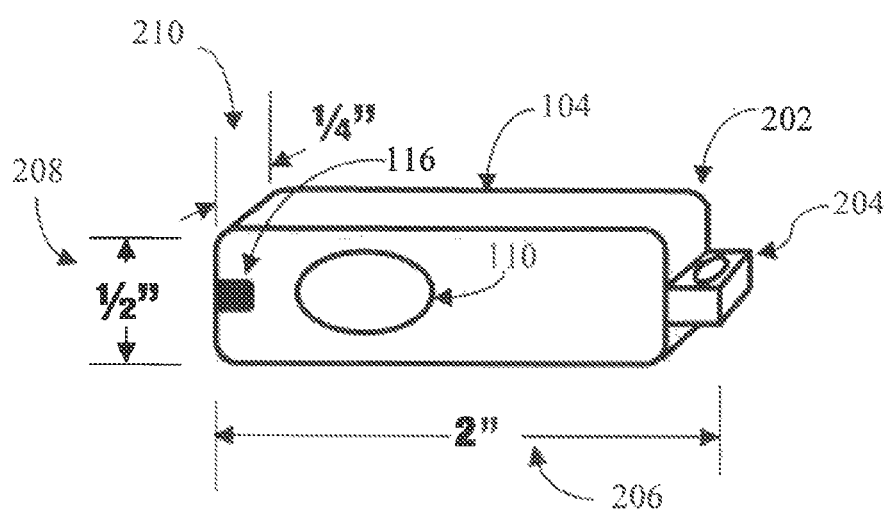
FIG. 2 is an elevational view of an exemplary SPARC Security Device 104 of FIG. 1, in accordance with an embodiment of the present invention.

FIG. 2 is a mechanical diagram for an exemplary SPARC Security Device 104 described with reference to FIG. 1, wherein a containment portion 202 provides containment of associated electrical and mechanical devices.

SPARC Security Device 104 may take a wide variety of physical forms, including but not limited to a bracelet, a ring, a key ring device, a pin-on device, a pocket device such as a pen, a set top programmable remote control device, or any similar lightweight and compact devices. SPARC Security Device 104 may be configured such that, when its power 120 runs low, an alarm is generated. The alarm may be an audible alarm, a visual alarm, or a vibration of the SPARC Security Device 104. Similarly, when someone attempts to use SPARC Security Device 104 with no accompanying or available communications network, an alarm can be generated. Preferably, the alarm is kept local, but includes within its range the Smart Device 102 with which the SPARC Security Device 104 is communicating.

SPARC Security Device 104 includes a button/sensor portion 110, an indicator portion 116, a containment portion 202, and an attachment element 204.

Use of the button 110 without an SD 102 input activates a pre-specified SD 102 application program on the corresponding Smart Device 102. Button 110 may comprise a biometric sensing actuating device. SSD 104 may not require an actuator at all; in this scenario, SSD 104 gives its SSD ID to the Smart Device automatically, as long as the distance requirement is satisfied.

Indicator 116 can have several different settings, corresponding to several different applications.

Containment portion 202 provides mechanical containment of associated electronic and mechanical devices associated with SPARC Security Device 104. Containment portion 202 has a length 206, a height 208, and a width 210. As a non-limiting example, length 206 may be two inches, height 208 may be ½ inch, and width 210 may be ¼ inch.

Attachment element 204 provides capability for attachment of SPARC Security Device 104 to other devices. Element 204 can be, e.g., a keychain, key ring, safety pin for attachment to clothing, etc.

Figure 3:
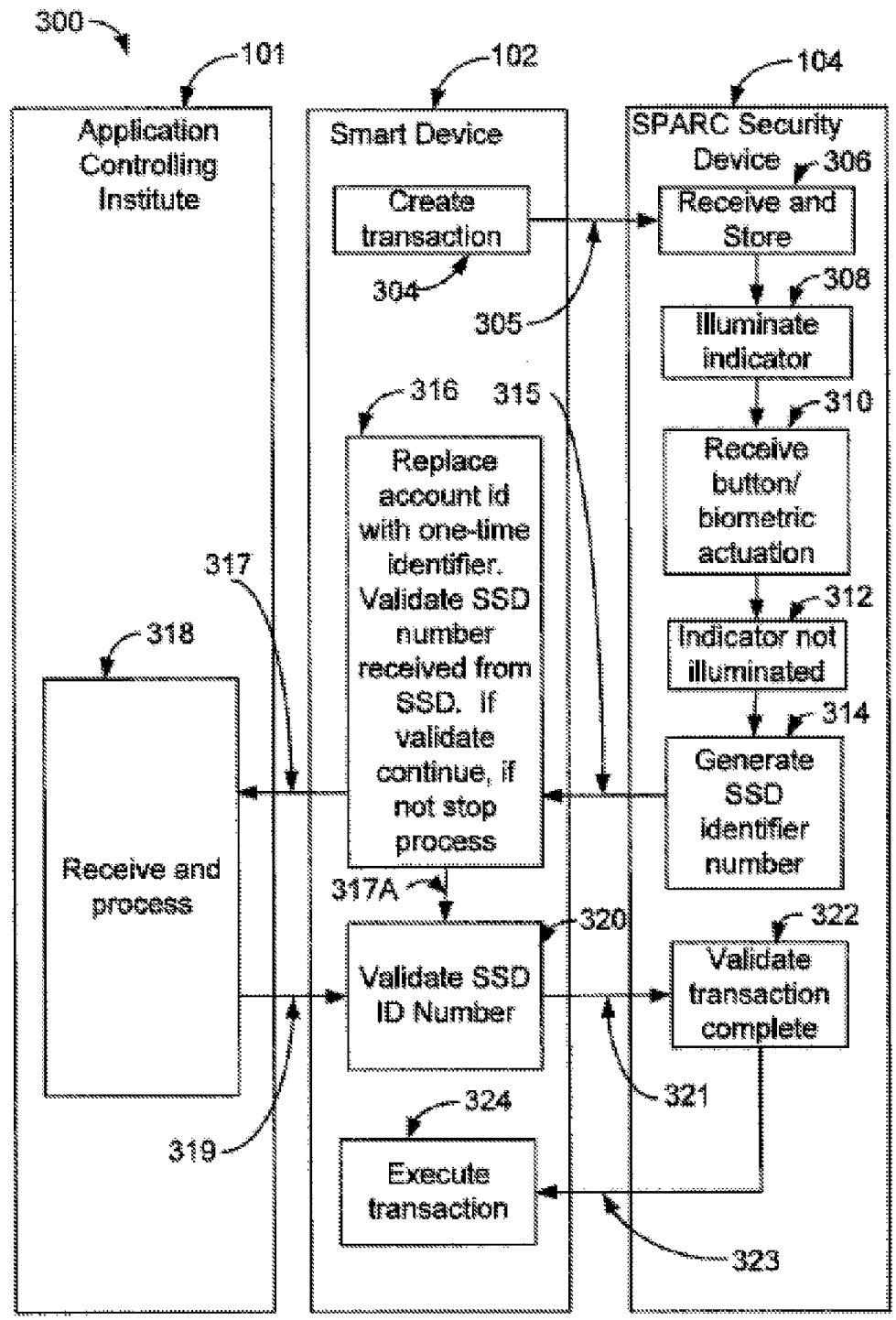
FIG. 3 is a block/flow diagram of an exemplary method for using the communication system described with reference to FIGS. 1 and 2, in accordance with an embodiment of the present invention.

FIG. 3 is a flow diagram of an exemplary communication system described with reference to FIG. 1-2, wherein a transaction associated with an Application Controlling Institution 101, Smart Device 102, and SPARC Security Device 104 is securely executed.

With reference to FIG. 3, a flow diagram 300 presents the communication flow between and among Application Controlling Institution 101, Smart Device 102, and SPARC Security Device 104.

Let us assume that an application associated with Smart Device 102 wishes to request a transaction with Application Controlling Institution 101. Non-limiting examples of information communicated from Smart Device 102 to Application Controlling Institution 101 include an account identifier, an Application Controlling Institution 101 designation, transaction type, fund type requested, requested fund amount, currency type (e.g., U.S. dollars), Smart Device 102 communications address, and a transaction password for routine security.

With reference to step 304, the user of SD 102 initiates this transaction via selection of a transmit button on SD 102 or via a SEND function on the associated application. Smart Device 102 communicates certain information (see line 305) to SPARC Security Device 104 over logical line 305. Non-limiting examples of this information that is communicated to SSD 104 include account identifier and transaction type.

At step 306, SPARC Security Device 104 stores in its memory the received account identifier and transaction type. At step 308, SPARC Security Device 104 illuminates its indicator portion 116, signaling the user to verify that the transaction should proceed. At step 310, SPARC Security Device 104 receives an indication that its user has actuated button/sensor 110. At step 312, illumination of indicator portion 116 is terminated.

At step 314, the SSD ID identifier is created by SPARC Security Device 104. This SSD ID identifier is communicated to Smart Device 102 over logical line 315.

At step 316, Smart Device 102 receives and validates the unique SSD ID received from SSD 104. If valid, the process continues. If not, the process terminates. Furthermore, Smart Device 102 communicates the SSD ID and the requested transaction to Application Controlling Institution 101 over logical line 317. All or part of the SSD ID can be stored in SD 102, to detect attacks involving use of a counterfeit SSD 104.

At step 318, ACI 101 receives and processes this information. ACI 101 uses the SPARC Security Device 104 unit identifier for retrieving information from its database indexed by the SSD 104 unit identifier. Furthermore, ACI 101 performs a comparison of the retrieved transaction identifier information with transaction identifier information in its database in order to verify that information received over line 317 is valid. Furthermore, Smart Device 102 can also validate the information received over line 317 via the date, time, ACI 101, and/or subject matter fields in the SSD ID.

Smart Device 102 then retrieves a user account identifier from its database via line 317A for performing the transaction processing.

If ACI 101 validates the transaction, ACI 101 processes the transaction. ACI 101 prepares and communicates any relevant information to Smart Device 102 over logical line 319. As a non-limiting example, the information sent over line 319 includes the unique SPARC Security Device 104 unit identifier.

At step 320, Smart Device 102 validates the transaction using information received over logical line 317A. Smart Device 102 transmits information over logical line 321 to SPARC Security Device 104 to complete the validation. Information sent over logical line 317A constitutes a copy of information sent over logical line 317, to validate the return message from the ACI 101.

At step 322, SPARC Security Device 104 completes validation of the transaction. As a non-limiting example, SPARC Security Device 104 validates that the received unique SSD 104 unit identifier is correct. Furthermore, SSD 104 communicates information over logical line 323 to Smart Device 102. As a non-limiting example, information sent over logical line 323 includes a signal authorizing Smart Device 102 to execute the transaction. As a non-limiting example, executing the transaction may include moving funds associated with a bank account.

At step 324, Smart Device 102 executes the transaction. As a non-limiting example, Smart Device 102 posts funds received from ACI 101.

Figure 4A:
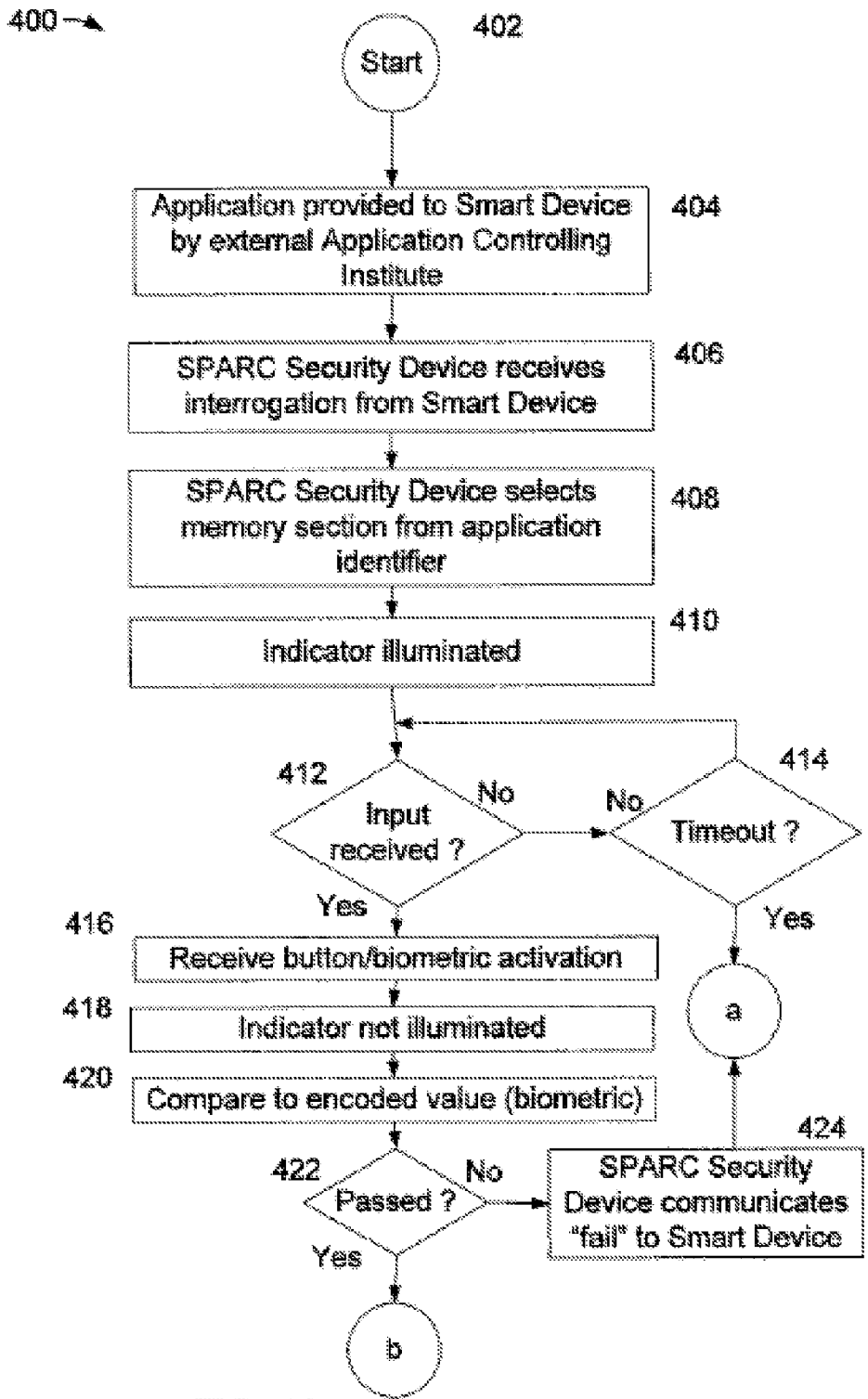
FIGS. 4A through 4C constitute a flow diagram illustrating an example of a method for using the communication system as described with reference to FIGS. 1-3, in accordance with an embodiment of the present invention.
Figure 4B:
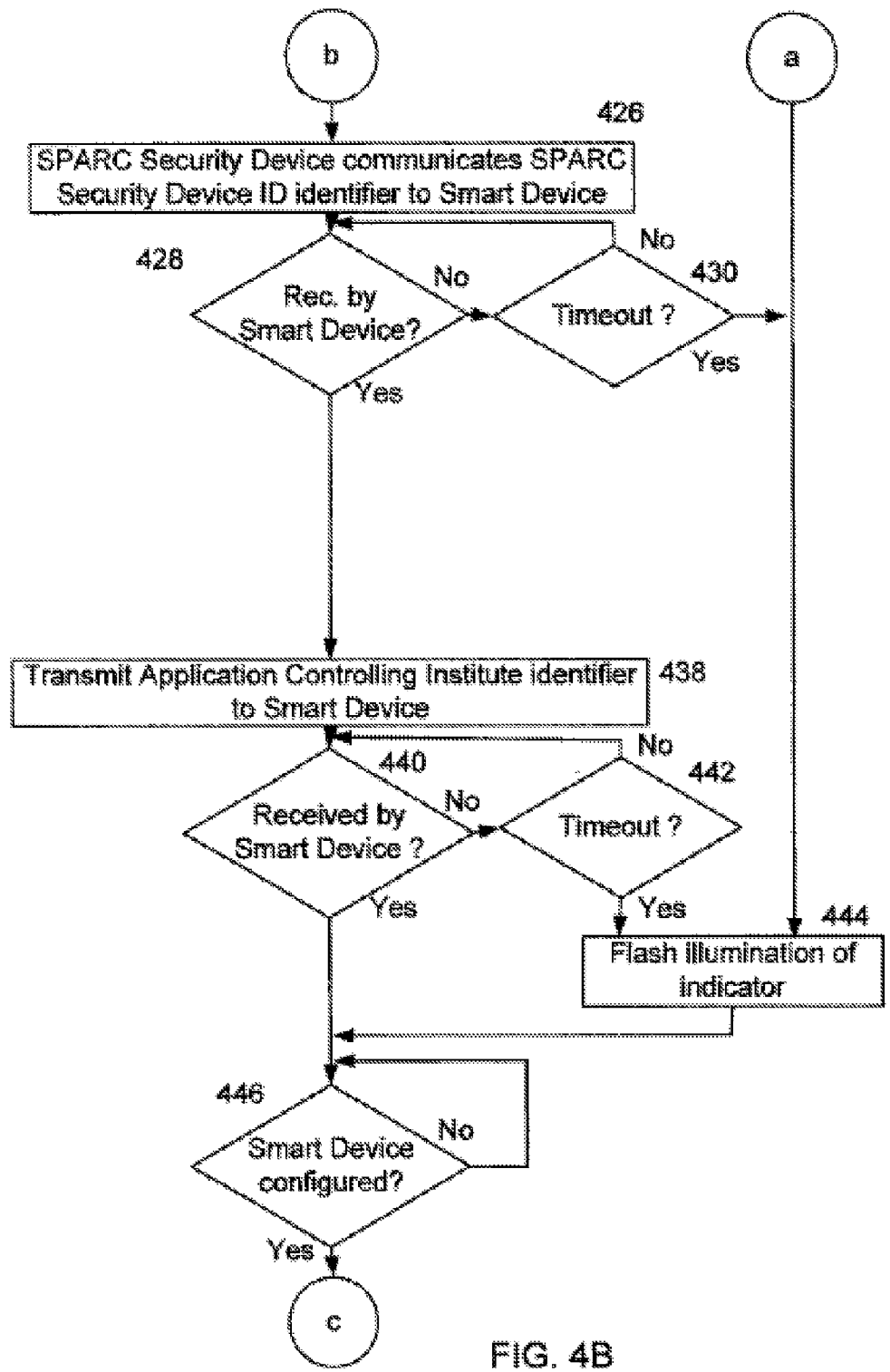
Figure 4C:
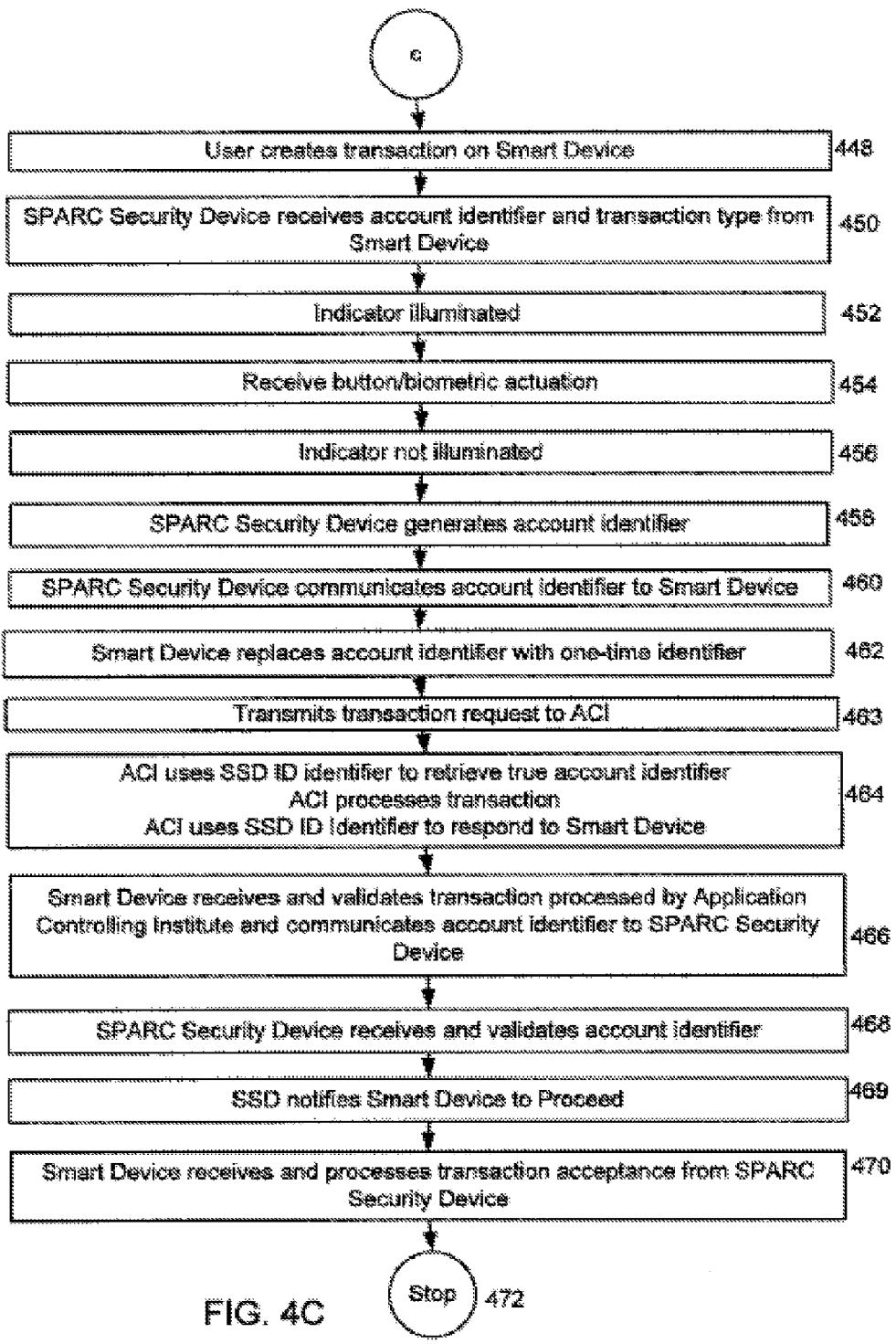

FIGS. 4A through 4C illustrate an exemplary method for using the secure communication system as described with reference to FIGS. 1 through 3, in accordance with an embodiment of the present invention.

Referring to FIG. 4A, method 400 initiates in step 402.

In step 404, an application is provided to Smart Device 102 by Application Controlling Institution 101. As a non-limiting example, Smart Device 102 receives an application from Application Controlling Institution 101 via communication channel 108.

In step 406, SPARC Security Device 104 receives an interrogation from Smart Device 102. As a non-limiting example, SPARC Security Device 104 (FIG. 1) receives an interrogation message from Smart Device 102 (FIG. 1) via communication channel 106.

In step 408, SPARC Security Device 104 selects its memory 112 section associated with the application identifier for the received application. As a non-limiting example, SPARC Security Device 104 (FIG. 1) selects a memory section associated with memory portion 112 (FIG. 1) associated with the application identifier.

In step 410, an indicator is illuminated. As a non-limiting example, indicator portion 116 (FIGS. 1-2) is illuminated.

In step 412, a determination for input received from button/sensor 110 is performed. For a determination of "no input received" in step 412, in step 414 a determination for a timeout condition is performed. For a determination of "no timeout" in step 414, the execution of method 400 transitions to step 412. For a determination of "an input received" in step 412, in step 416, activation associated with button/sensor 110 is received by SPARC Security Device 104. As a non-limiting example, processor portion 114 (FIG. 1) receives an indication from button/sensor portion 110 (FIG. 1) via communication channel 122 (FIG. 1).

In step 418, illumination of an indicator is terminated. As a non-limiting example, illumination of indicator portion 116 (FIG. 1) is terminated.

In step 420, a comparison is performed between received biometric information and stored biometric information to authenticate that an authorized user is performing actuation of sensor. As a non-limiting example, biometric information (e.g., a fingerprint) provided by button/sensor portion 110 (FIG. 1) is compared with biometric information stored in memory portion 112 (FIG. 1) by processor portion 114 (FIG. 1).

In step 422, a determination for pass/fail for the biometric comparison performed in step 420 is made. For a determination of "fail" in step 422, in a step 424, SPARC Security Device 104 communicates a failure message to Smart Device 102. As a non-limiting example, SPARC Security Device 104 (FIG. 1) communicates a failure message to Smart Device 102 (FIG. 1) via communication channel 106 (FIG. 1). For a determination of "pass" in step 422, in step 426, illustrated with reference to FIG. 4B, SPARC Security Device 104 communicates its unique SPARC Security Device unit identifier to Smart Device 102. As a non-limiting example, SPARC Security Device 104 (FIG. 1) communicates the unique unit identifier associated with SPARC Security Device 104 (FIG. 1) to Smart Device 102 (FIG. 1).

In step 428, a determination for Smart Device 102 receiving SPARC Security Device unit identifier from SPARC Security Device 104 is performed. For a determination of Smart Device 102 not receiving the unique SPARC Security Device 104 unit identifier in step 428, in step 430, a determination for a timeout condition is performed. For a determination of "not a timeout condition" in step 430, the execution of method 400 transitions to step 428. For a determination of receiving the unique SPARC Security Device 104 unit identifier in step 428, in step 438, the Application Controlling Institution 101 identifier is communicated from Application Controlling Institution 101 to Smart Device 102.

In step 440, a determination for receipt of the Application Controlling Institution 101 identifier is performed by Smart Device 102. For a determination of not receiving Application Controlling Institution 101 identifier by Smart Device 102 in step 440, in step 442, a determination for a timeout condition is performed. For a determination of "not a timeout condition" in step 442, the execution of method 400 transitions to step 440.

Following SPARC Security Device 104 communicating a "fail" to Smart Device 102 in step 424 (FIG. 4A), determination of a timeout in step 414 (FIG. 4A), step 430 (FIG. 4B) and 442 (FIG. 4B), in a step 444 (FIG. 4B) indicator portion 116 (FIGS. 1-2) is illuminated in a flashing manner.

Following flash illumination of the indicator in step 444 and for a determination of receiving an Application Controlling Institution 101 identifier in step 440, in step 446, a determination for a properly configured Smart Device 102 is performed.

For a determination of a "not configured Smart Device 102" in step 446, the execution of method 400 returns to step 446.

For a determination of a properly configured Smart Device 102 in step 446, in step 448, as illustrated with reference to FIG. 4C, the user creates a transaction on Smart Device 102 (FIG. 1) as described with reference to step 304 (FIG. 3).

In step 450, SPARC Security Device 104 receives an account identifier and transaction type from Smart Device 102. In some embodiments, response to the transaction request may be discrete data or a continuous data stream, or both.

As a non-limiting example, SPARC Security Device 104 (FIG. 1) receives an account identifier and transaction type from Smart Device 102 (FIG. 1) as described with reference to step 306 (FIG. 3).

In step 452, an indicator is illuminated. As a non-limiting example, indicator portion 116 (FIGS. 1-2) is illuminated as described with reference to step 308 (FIG. 3).

In step 454, SPARC Security Device 104 receives actuation information associated with a button or sensor. As a non-limiting example, processor portion 114 (FIG. 1) receives information associated with actuation of button/sensor portion 110 (FIG. 1) via communication channel 122 (FIG. 1) as described with reference to step 310 (FIG. 3).

In step 456, illumination of an indicator is terminated as described with reference to step 314 (FIG. 3).

Then in step 458, SPARC Security Device 104 generates an SSD ID as described with reference to event 314 (FIG. 3).

In step 460, SPARC Security Device 104 communicates the SSD ID to Smart Device 102 as described with reference to step 315 (FIG. 3).

In step 462, Smart Device 102 replaces the SSD ID with the one-time SSD ID as described with reference to step 316 (FIG. 3). In step 463, Smart Device 102 transmits a transaction request to ACI 101.

In step 464, Application Controlling Institution (ACI) 101 uses the SSD ID to retrieve the user's account number. ACI 101 processes the transaction if valid. In some embodiments, a transaction request passes through the ACI 101 to a second ACI 101 for evaluation or action. ACI 101 uses the SSD ID identifier to respond to Smart Device 102 with reference to step 318 (FIG. 3).

In step 466, Smart Device 102 receives and validates the transaction processed by Application Controlling Institution 101, and communicates the SSD ID to SPARC Security Device 104 as described with reference to step 320 (FIG. 3).

In step 468, SPARC Security Device 104 receives and validates a second one-time SSD ID as described with reference to step 322 (FIG. 3). In step 469, SPARC Security Device 104 notifies Smart Device 102 to proceed.

In step 470, Smart Device 102 receives and processes transaction acceptance from SPARC Security Device 104 as described with reference to step 324 (FIG. 3).

In step 472, execution of method 400 terminates.

Figure 5:
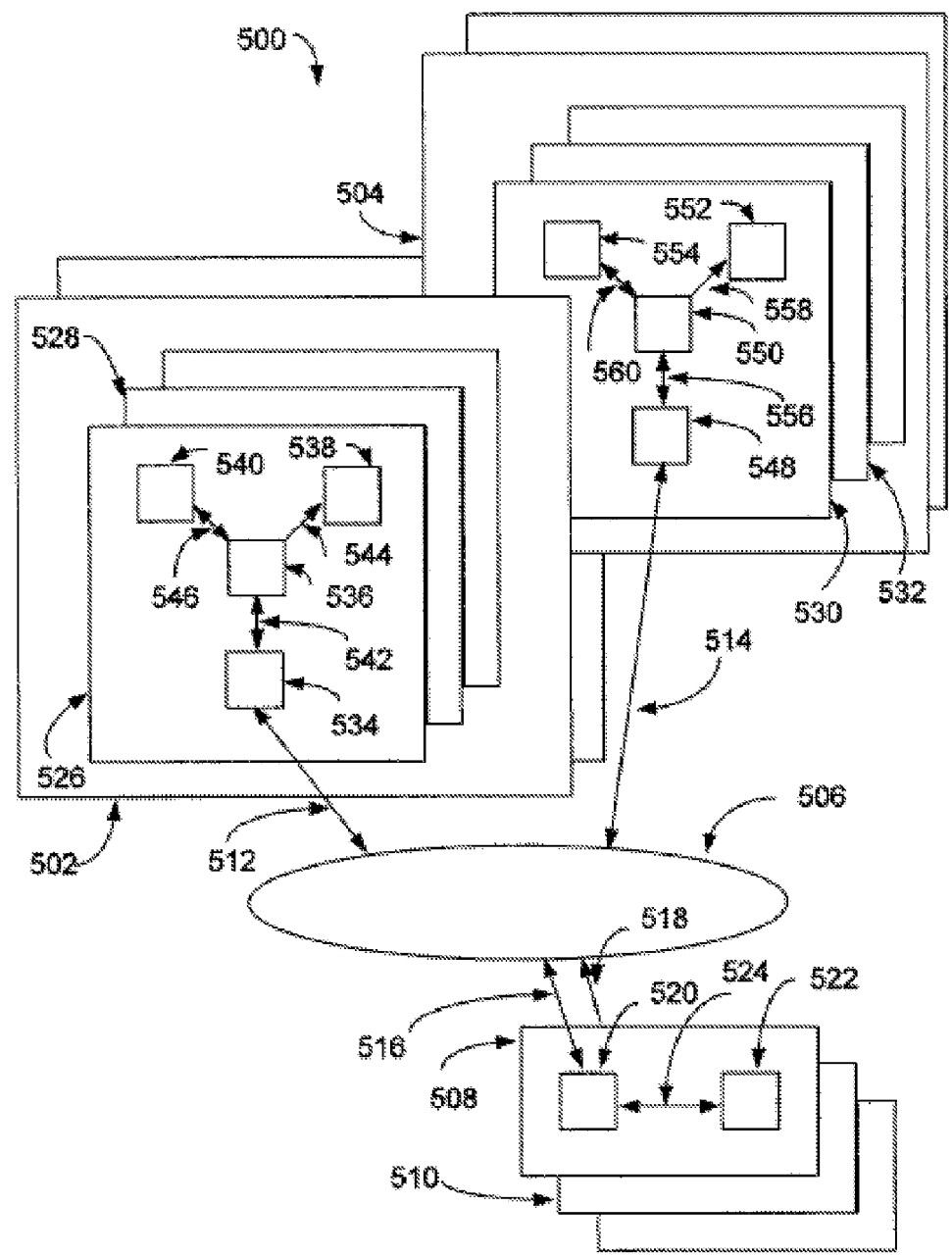
FIG. 5 is a block diagram depicting a conventional client/server communication system, over which the present invention can operate.

FIG. 5 is a block diagram depicting a conventional client/server communication system, over which the present invention can operate.

With reference to FIG. 5, communication system 500 includes a multiplicity of networked regions, with a sampling of regions denoted as network region 502 and network region 504, global network 506, and a multiplicity of servers, with a sampling of servers denoted as server device 508 and server device 510.

Network region 502 and network region 504 can be adapted to operate to represent a network contained within a geographical area or region. Non-limiting examples of representations for the geographical areas for the networked regions include postal zip codes, telephone area codes, states, counties, cities, and countries. Elements within network regions 502 and 504 can communicate with external elements within other networked regions, or within elements contained within the same network region 502, 504.

In some implementations, global network 506 is adapted to operate as the Internet.

It will be understood by those skilled in the art that communication system 500 may take many different forms. Non-limiting examples of forms for communication system 500 include local area networks (LANs), wide area networks (WANs), wired telephone networks, cellular telephone networks, or any other network that supports data communication between and among respective entities via hardwired or wireless communication networks. Global network 506 may operate to transfer information between or among the various networked elements.

Server device 508 and server device 510 are adapted to operate to execute software instructions, store information, support database operations, and communicate with other networked elements. Non-limiting examples of software and scripting languages which can be executed on server device 508 and server device 510 include C, C++, C#, and Java.

Network region 502 can be adapted to operate to communicate bi-directionally with global network 506 via communication channel 512. Similarly, network region 504 can be adapted to operate to communicate bi-directionally with global network 506 via communication channel 514. Server device 508 can be adapted to operate to communicate bi-directionally with global network 506 via communication channel 516. Similarly, server device 510 can be adapted to operate to communicate bi-directionally with global network 506 via communication channel 518. Network regions 502 and 504, global network 506, and server devices 508 and 510 can be adapted to operate to communicate bi-directionally with each other, and also communicate bi-directionally with other networked devices located within communication system 500.

Server device 508 includes a networking device 520 and a server 522. Networking device 520 can be adapted to operate to communicate bi-directionally with global network 506 via communication channel 516, and with server 522 via communication channel 524. Server 522 can execute software instructions and store information.

Network region 502 includes a multiplicity of computing devices, with sample clients denoted as client 526 and client 528. Client 526 includes a networking device 534, a processor 536, a GUI 538, and an interface device 540. Non-limiting examples of devices for GUI 538 include monitors, televisions, cellular telephones, smartphones, and PDAs (Personal Digital Assistants). Non-limiting examples of interface device 540 include a pointing device, mouse, trackball, scanner, and printer. Networking device 534 may communicate bi-directionally with global network 506 via communication channel 512 and with processor 536 via communication channel 542. GUI 538 may receive information from processor 536 via communication channel 544 for presentation to a user for viewing. Interface device 540 can send control information to processor 536 and receive information from processor 536 via communication channel 546.

Similarly, network region 504 includes a multiplicity of client computing devices, with sample clients denoted as client 530 and client 532. Client 530 includes a networking device 548, a processor 550, a GUI 552, and an interface device 554. Non-limiting examples of devices for GUI 538 include monitors, televisions, cellular telephones, smartphones, and PDAs (Personal Digital Assistants). Non-limiting examples of interface device 540 include pointing devices, mice, trackballs, scanners, and printers. Networking device 548 may communicate bi-directionally with global network 506 via communication channel 514, and with processor 550 via communication channel 556. GUI 552 may receive information from processor 550 via communication channel 558 for presentation to a user for viewing. Interface device 554 can send control information to processor 550 and receive information from processor 550 via communication channel 560.

For example, consider the case where a user interfacing with client 526 wants to execute a networked application. A user enters the IP (Internet Protocol) address for the networked application using interface device 540. The IP address information is communicated to processor 536 via communication channel 546. Processor 536 then communicates the IP address information to networking device 534 via communication channel 542. Networking device 534 then communicates the IP address information to global network 506 via communication channel 512. Global network 506 then communicates the IP address information to networking device 520 of server device 508 via communication channel 516. Networking device 520 then communicates the IP address information to server 522 via communication channel 524. Server 522 receives the IP address information, and after processing the IP address information, communicates return information to networking device 520 via communication channel 524. Networking device 520 communicates the return information to global network 506 via communication channel 516. Global network 506 communicates the return information to networking device 534 via communication channel 512. Networking device 534 communicates the return information to processor 536 via communication channel 542. Processor 536 communicates the return information to GUI 538 via communication channel 544. The user then views the return information on GUI 538.

Figure 6:
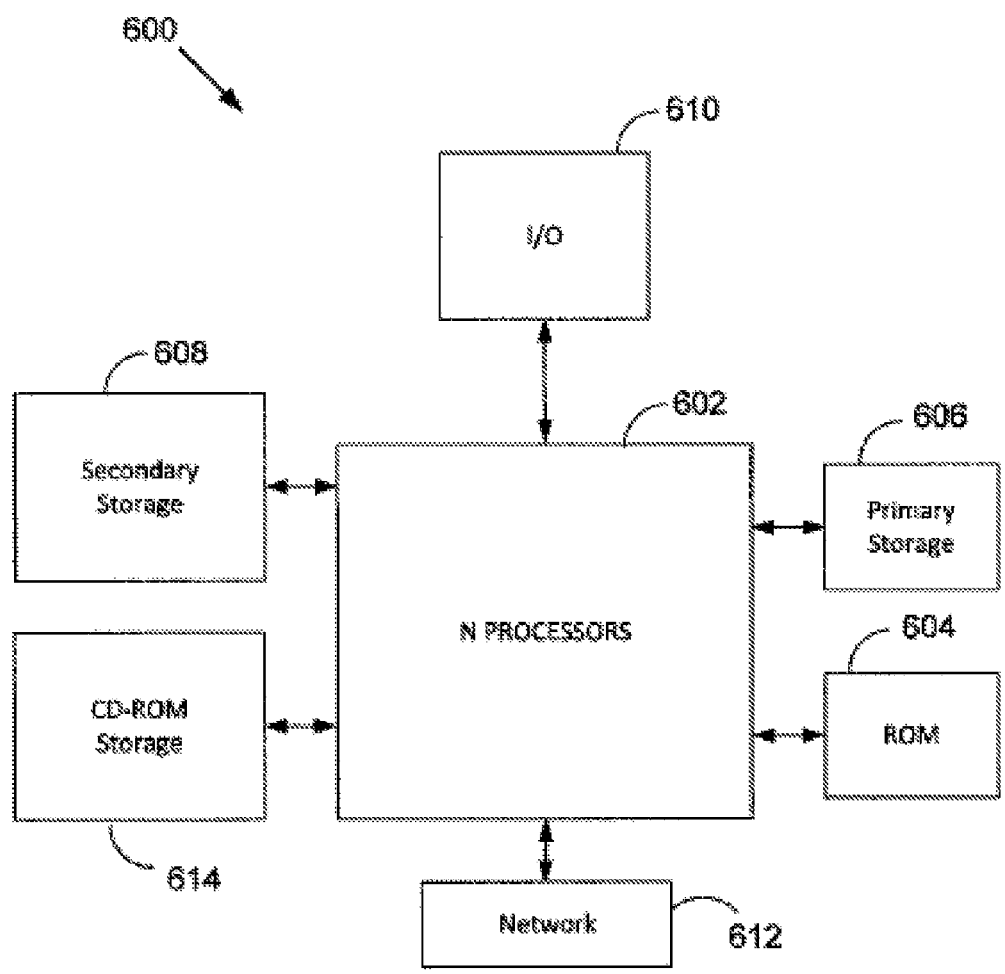
FIG. 6 is a block diagram of a typical computer system that, when appropriately configured or designed, can serve as a computer system 600 in which the present invention may be embodied.

FIG. 6 illustrates a typical computer system that, when appropriately configured or designed, can serve as a computer system 600 for which the present invention may be embodied.

With reference to FIG. 6, computer system 600 includes a quantity of processors 602 (also referred to as central processing units, or CPUs) that are coupled to storage devices including a primary storage 606 (typically a random access memory, or RAM), and a primary storage 604 (typically a read-only memory, or ROM). CPU 602 may be of various types, including micro-controllers (e.g., with embedded RAM/ROM) and microprocessors such as programmable devices (e.g., RISC or SISC based, or CPLDs and FPGAs), and devices not capable of being programmed, such as gate array ASICs (Application Specific Integrated Circuits) or general purpose microprocessors. As is well known in the art, primary storage 604 acts to transfer data and instructions uni-directionally to the CPU, and primary storage 606 typically is used to transfer data and instructions in a bi-directional manner. The primary storage devices discussed previously can include any suitable computer-readable media, such as those described above. A mass storage device 608 can also be coupled bi-directionally to CPU 602, provides additional data storage capacity, and can include any of the computer-readable media described above. Mass storage device 608 can be used to store programs, data, and the like, and typically is used as a secondary storage medium, such as a hard disk. It will be appreciated that the information retained within mass storage device 608 can, in appropriate cases, be incorporated in standard fashion as part of primary storage 606 as virtual memory. A specific mass storage device such as a CD-ROM 614 can also pass data uni-directionally to the CPU.

CPU 602 can also be coupled to an interface 610 that connects to one or more input/output devices, such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computing devices. Finally, CPU 602 optionally can be coupled to an external device, such as a database or a computer or telecommunications or Internet network using an external connection shown generally as a network 612, which can be implemented as a hardwired or wireless communications link using suitable conventional technologies.

With such a connection, the CPU can receive information from the network, or output information to the network in the course of performing the method steps described in the teachings of the present invention.

Figure 7A:
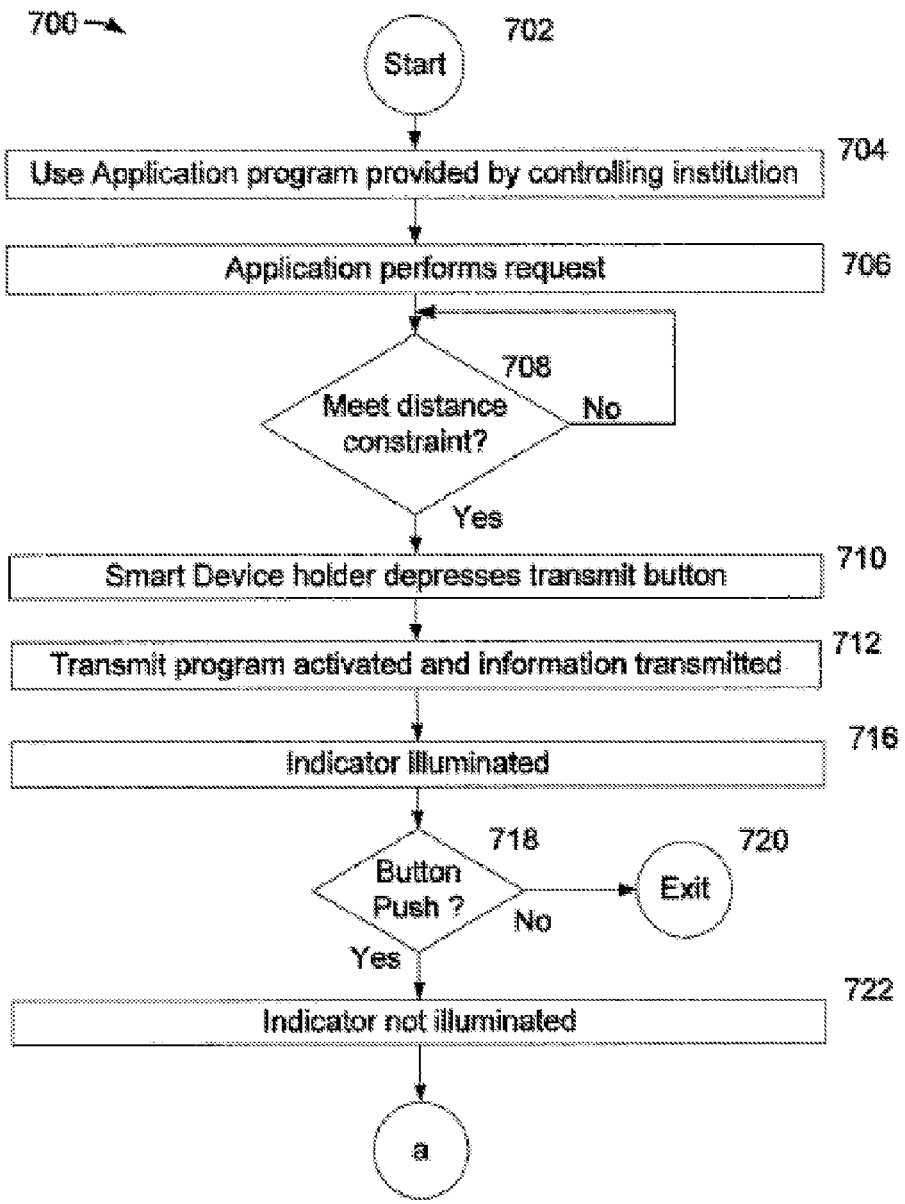
FIGS. 7A and 7B constitute a flow diagram illustrating an example of a method for using the communication system as described with reference to FIGS. 1-3, in accordance with an embodiment of the present invention.
Figure 7B:
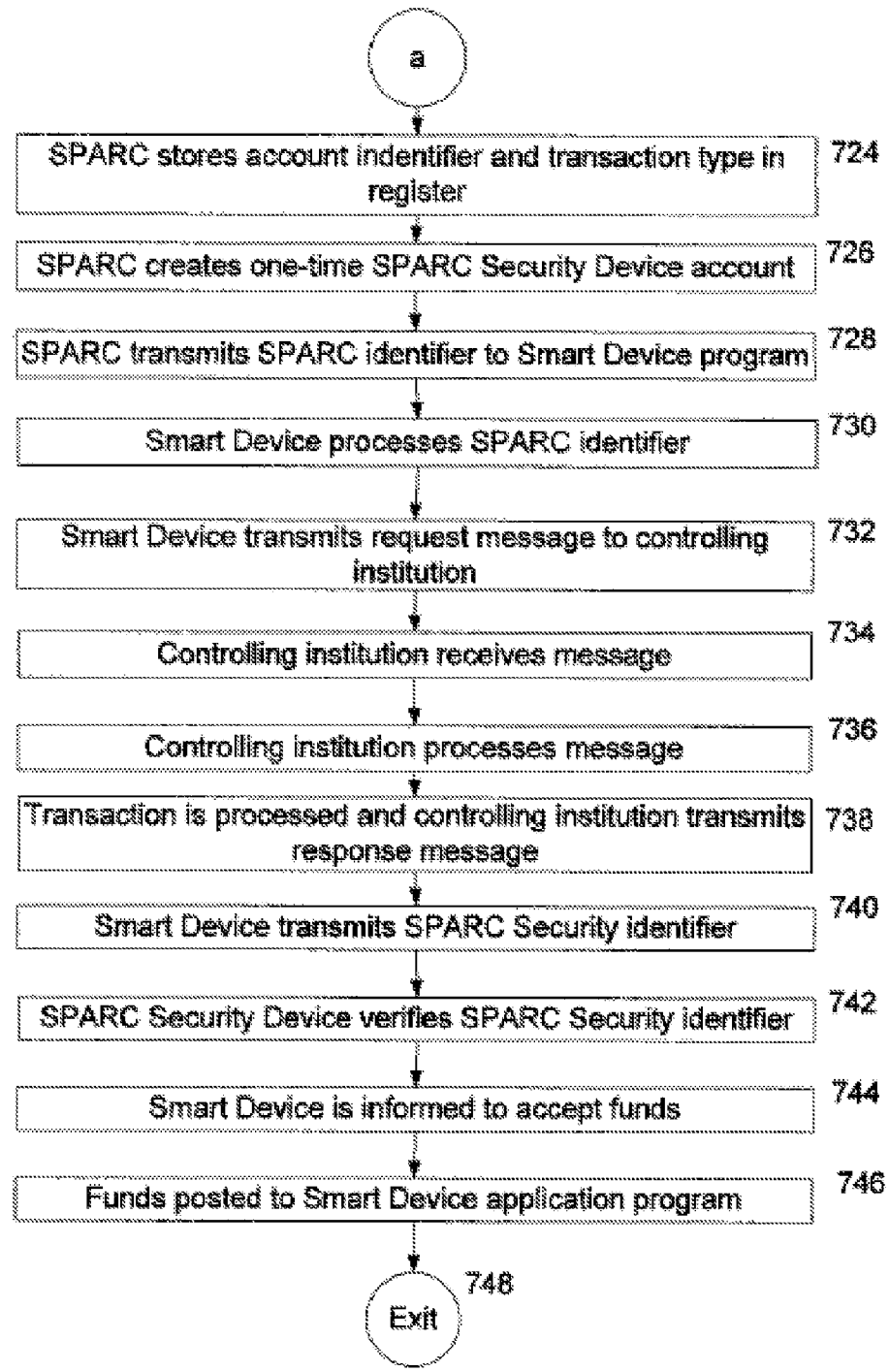

FIGS. 7A and 7B illustrate an exemplary method for using the secure communication system as described with reference to FIGS. 1 through 3, in accordance with an embodiment of the present invention.

Method 700 initiates in step 702.

Then in step 704, Smart Device 102 uses an application program provided by a control center. As a non-limiting example, Smart Device 102 (FIG. 1) initiates operation of an application provided by Application Controlling Institution 101 (FIG. 1).

In step 706, the application performs a request. As a non-limiting example, Smart Device 102 (FIG. 1) transmits a request for crediting Smart Device 102 funds of $200 from Application Controlling Institution 101 (FIG. 1). Non-limiting examples of information communicated include an account identifier, institution designation, transaction type (e.g., funds request), requested funds amount, currency type (e.g. U.S. dollars), Smart Device's communications address, and a transaction password provided for routine security.

In step 708, a determination is performed as to whether a pre-established distance constraint is met. As a non-limiting example, the distance between SPARC Security Device 104 (FIG. 1) and Smart Device 102 (FIG. 1) is determined to be within a pre-established distance constraint. As a non-limiting example, the devices may be required to be less than Near Field Communications (NFC) distance (roughly 4 inches).

In step 710, a person holding Smart Device 102 depresses a transmit button. As a non-limiting example, a person depresses button/sensor portion 110 (FIG. 1), as the Smart Device 102 has some or all of the same controls as an SSD 104.

In step 712, a transmit program is activated and information is transmitted. As a non-limiting example, a program for transmitting information from Smart Device 102 (FIG. 1) to SPARC Security Device 104 (FIG. 1) is activated, and information is transmitted from Smart Device 102 (FIG. 1) to SPARC Security Device 104 (FIG. 1). Non-limiting examples of information transmitted include instructions to activate indicator portion 116 (FIG. 1), select button/sensor portion 110 (FIG. 1), deactivate indicator portion 116 (FIG. 1); an account identifier; and a transaction type.

In step 716, an indicator is illuminated. As a non-limiting example, indicator portion 116 (FIG. 1) is activated.

In step 718, a determination for selecting a button is performed. As a non-limiting example, a determination for selection of button/sensor portion 110 (FIG. 1) is performed.

For a determination of not pushing the button in step 718, execution of method 700 is terminated in step 720. As a non-limiting example, for a determination of not selecting button/sensor portion 110 (FIG. 1) within a preselected period of time, execution of method 700 is terminated in step 720.

For a determination of pushing the button in step 718, in step 722, an indicator is not illuminated. As a non-limiting example, indicator portion 116 (FIG. 1) is deactivated.

In step 724, a security device stores an account identifier and transaction type in a register. As a non-limiting example, SPARC Security Device 104 (FIG. 1) stores an account identifier and a transaction type in a register.

In step 726, a security device creates a one-time security device account. As a non-limiting example, SPARC Security Device 104 (FIG. 1) creates a one-time SSD ID. As a non-limiting example, the SSD ID includes a SPARC transaction code, a SPARC unit number, the current date, the current time, and a one-time transaction identifier.

In step 728, a security device transmits an identifier to a smart device program. As a non-limiting example, SPARC Security Device 104 (FIG. 1) transmits an SSD ID to a program executing on Smart Device 102 (FIG. 1).

In step 730, a smart device processes an identifier. As a non-limiting example, Smart Device 102 (FIG. 1) replaces an account identifier in a request message with the SSD ID.

In step 732, a smart device transmits a request message to a control center. As a non-limiting example, Smart Device 102 (FIG. 1) transmits a request message to Application Controlling Institution 101 (FIG. 1).

In step 734, the control center receives the message. As a non-limiting example, Application Controlling Institution 101 (FIG. 1) receives the message from Smart Device 102 (FIG. 1).

Referring to FIG. 7B, in step 736, the control center processes the message. As a non-limiting example, Application Controlling Institution 101 (FIG. 1), recognizes the SSD ID, and uses the unique SPARC 104 unit identifier for database lookup. Furthermore, the result of the lookup provides a transaction identifier. Furthermore, a transaction identifier comparison validates the message. In some embodiments, an application may validate the date and time for further validation processing. Furthermore, a database associated with ACI 101 provides an account identifier for transaction processing. The primary purpose of the database is to store the true account number corresponding to the SSD ID. In some alternate embodiments, a non-limiting additional use of the ACI 101 database is to store a "Personal Profile" and "Preferences" for the SSD 104 user. The Personal Profile describes the physical, educational, and societal background of the SSD 104 user. The Preferences section is a non-limiting list of the data streams for which the user wants to stay up-to-date. Non-limiting examples include Google Alerts®, select stock markets, RSS feeds, and Google Ads®. Including the results of these additional data streams offers a revenue opportunity to the ACI 101, and an improved data flow for the SSD 104 user.

In step 738, the transaction is processed and the control center transmits a response message. As a non-limiting example, Application Controlling Institution 101 (FIG. 1) processes the message and generates a response message. As a non-limiting example, the response message includes the unique SSD 104 unit identifier used for Smart Device 102 (FIG. 1) to perform validation.

In step 740, a smart device transmits an identifier. As a non-limiting example, Smart Device 102 (FIG. 1) transmits the received SSD 104 unit identifier to SPARC Security Device 104 (FIG. 1) for evaluation.

In step 742, a security device verifies the identifier. As a non-limiting example, SPARC Security Device 104 (FIG. 1) establishes that the received SSD 104 unit identifier is correct.

In step 744, the smart device is informed to accept funds. As a non-limiting example, SPARC Security Device 104 (FIG. 1) informs Smart Device 102 (FIG. 1) to accept the funds.

In step 746, funds are posted to a smart device application program. As a non-limiting example, funds are posted to the application program associated with Smart Device 102 (FIG. 1).

In step 748, execution of method 700 terminates.

Use of the unique SSD 104 unit identifier with the one-time transaction number in place of an account number makes content meaningless to those overhearing the communications.

If an incorrect transaction number is received, the receiving entity 101, 102, 104 normally erases or destroys the message as being fraudulent, because an incorrect transaction number is an indication of fraud. Such a message may contain a virus or other malware. In this case, the receiving SD 102 or SSD 104 sends a notice to the ACI 101.

An incorrect value in the one-time transaction number indicates a fraudulent download. Any of the three types of devices 101, 102, 104 described in this secure communications system could send a message with an incorrect SSD number or transaction number. In that case, the other two devices conclude that something is awry.

The processes described herein pertaining to the SSD 104 may replace the customary bank card, PIN number, and keyboarding that one uses when withdrawing cash from an ATM (Automated Teller Machine). In these embodiments, the ATM is controlled by an ACI 101.

The combination of the SD 102 and the SSD 104 can provide identification and access control for any number of industries, including medical, retail, supermarket, government, education, student, and travel.

The SSD 104 processes described herein may be incorporated as the basis for a revenue producing insurance program, in which screening for valid messages is done by an ACI 101 or an SSD 104. In this embodiment of the present invention, SD 102 first establishes a "white list" of acceptable correspondents and/or types of messages for whom it wishes to send or receive messages. SD 102 conveys this white list to ACI 101 and/or SSD 104, which screen messages sent to SD 102 adhering to the criteria of the white list. ACI 101, for an appropriate insurance premium that it charges to the user of SD 102, insures said user that only acceptable types of messages, to or from acceptable correspondents, are sent to or received from SD 102.

In one embodiment, independent of the usage of the SSD 104, when an SD 102 is used with a magnetic stripe reader (for example, one provided by the company Square), two messages are produced by a software application within the SD 102. One of the messages corresponds to the user account number, and the other message pertains to the remaining content. "Remaining content" can comprise expiration date and/or bank number. This embodiment also can be used when two Smart Devices 102 are interacting with each other (e.g., in a chip interface). The interaction may be by physical contact, or by proximity in the case of protocols such as NFC.

The unique SSD 104 unit number is not stored on the Smart Device 102. This is a precaution, in case the SD 102 is lost or stolen. Conversely, one does not want to store user account numbers in the SSD 104, even if they are stored in the SD 102.

A message content check can be added to a message downloaded to SD 102 to detect any attempt to add a destructive program (for example, a virus) to the message. ("Downloaded" refers to a message that is received by the Smart Device 102.) In this case, the ACI 101 adds the same message content check for transaction messages that are received by SD 102. The message content check can comprise the SSD ID and/or something else.

The Smart Device 102 may be configured to require the cooperation of SSD 104 prior to any message being sent from SD 102. This can be accomplished by means of a lockout switch on SD 102.

This security feature can be strengthened even further by means of requiring that all incoming messages to, as well as all outgoing messages from, the SD 102 require cooperation of the corresponding SSD 104. Again, this can be accomplished by a switch, or can be hard-wired into the SD 102.

In these embodiments, the SSD 104 acts like an "ignition key" for the Smart Device 102. In other words, SD 102 is useless unless SSD 104 is present. The distance requirement still has to be met. In WiFi and Bluetooth, the battery in each of the SD 102 and SSD 104 has to be functioning. In the NFC protocol only one battery has to be functioning, in either SD 102 or SSD 104, because in the NFC protocol, the device with the non-functioning battery is powered by the RF signal over which SD 102 and SSD 104 communicate.

The SD 102 can comprise a holding buffer memory for containing incoming messages until validated by the associated SSD 104. In these embodiments, if the incoming message does not have the correct SSD ID, the message is destroyed by SD 102 on the grounds that there is a high possibility that the message contains malware.

Vital data in the SD 102 may be disguised and protected from external examination if the SD 102 is lost or stolen, by adding the unique unit number of the associated SSD 104 to each such vital data item.

One SSD 104 can be employed with multiple ACIs 101. In these embodiments, identifiers for the ACI 101 are stored in the SSD 104. The various ACIs 101 can represent different financial resources, such as Credit 1, Credit 2, Debit 1, Debit 2, Mortgage 1, Transfer 1, Travel, Point of Sale (POS), ATM (Automated Teller Machine). In these embodiments, the combination of the SD 102 and the SSD 104 constitutes a payment device, which can completely replace coins, paper currency, and credit or debit cards. The several ACIs 101 can share the single SSD 104 by means of sending ACI 101 to ACI 101 messages amongst themselves.

The SSD ID described herein replaces a PIN, a password, and encryption. Encryption can still be used at various places in this communications system for additional security or protection of vital data, but a downside with encryption is that it requires a relatively cumbersome key-management system.

In one embodiment, moving the Smart Device 102 out of the communications range of the associated SSD 104 causes an alarm to be activated. The alarm can be auditory, visual, and/or vibrational. In certain embodiments, any use of Smart Device 102 automatically triggers the "waking up" of the associated SSD 104.

Typically an ACI 101 to SSD 104 message contains only the SSD ID.

The SSD 104 security scheme described herein is compatible with security concepts used successfully for nearly 50 years for bank card security, i.e., use of a central database for security decisions. This is achieved by using the unique SSD 104 unit number for transaction authorization at the ACI 101. The ACI 101 database uses the SSD 104 unit number to look up the user account number for the transaction. This successfully removes the actual user account number from the transmitted data.

An important alternative for the format of the SSD ID is, but not limited to, to make said format consistent with the established database number in existing ACI 101 databases, namely the ANSI x4.16-1983 (ISO 3554) Magnetic Stripe Card, Track 2 Standard. In this Standard, the SSD ID content comprises 40 digits of 5 bits each, including a parity check bit. The primary ID number is 19 digits, including ACI 101 identification and the unique SSD 104 identification number. Also included are 17 digits of additional data comprising the one-time transaction number, and optional fields, such as the date, time, ACI 101 number, and any sub-account designation. The remaining bits comprise control and check digits. In this Track 2 Standard, the transaction number is truly a number, i.e., it is not an alphanumeric expression.

The processes described herein can be said to convert the security problem to a database process. In summary:

SD 102 performs these steps:
Actuate Smart Device 102 application. Select transaction and enter amount.
Actuate "Send" function. Send signal to SPARC Security device (SSD) 104.

Then SSD 104 performs these steps:
Receive signal. Ask user to actuate SSD 104.
Generate SSD ID, including one-time transaction number (TN).
Send SSD ID to SD 102.
Advance TN for next transaction. Each SSD 104 contains a unique algorithm for TN advance.

Then SD 102 performs these steps:
Receive SSD ID. Replace account number. Optionally, indicate sub-account.
Complete transaction message and send to Application Controlling Institution 101.

Then ACI 101 performs these steps:
Receive SD 102 message in its buffer.
Access database—retrieve account number, compare TN value with expected number.
If TN is OK, process message. If not, erase transaction and notify SD 102. Prepare response.
Advance TN and prepare SSD ID transmit reply message to SD 102.

Then SD 102 performs these steps:
Receive and hold message in SD 102 buffer. Send SSD ID to SSD 104.

Then SSD 104 performs these steps:
Evaluate SSD ID. If OK, advise SD 102 to process transaction. If not, destroy message.
Advance TN value for next message.

Then SD 102 performs these steps:
Process reply message content. Display result. Clear buffer.

Loyalty Applications

It can be highly desirable to apply the SSD 104 functionality described herein to perform and safeguard "Loyalty Applications". As used herein, a "Loyalty Application" is one which is principally used by a participating entity or a group of participating entities that share a common nomenclature, and a common set of objectives and practices; and that provide a common set of products or services, in exchange for earned income or loyalty. "Participating entities" can include, without limitation, one or more merchants, corporations, fraternal organizations, and/or nonprofit organizations. For example, the group of participating entities may be a chain of supermarkets, wherein the chain awards a bonus of $10 worth of groceries to users who purchase $200 worth of groceries at the chain in a given month. As another example, the participating entity may be a corporation that offers its employees incentive credits to use local health/wellness facilities, as a means for controlling its health care costs. As yet another example, the participating entity may be a charitable organization that wishes to make it easier for contributors to make charitable contributions to the organization.

An SSD 104 Loyalty Application can comprise the user of SD 102 and SSD 104 interacting with the process to purchase an article or to use a service so as to: (1) uniquely identify and provide the purchaser with a secure method to accept incentives offered by the entity or group of entities (including but not limited to inducements, rebates, loyalty points, or rewards from participating merchants, corporations, fraternal organizations, or nonprofit organizations, some of whom may not even be known to the user); (2) provide a purchasing or loyalty incentive based on the purchaser's or user's prior account relationship and actual account utilization with a preferred provider or group of providers, or through an ACI 101 member base; (3) capture the potential price or incentive value earned in response to selecting a Loyalty Application purchase decision or the use of a service; (4) provide the payment function associated with the selected Loyalty Application purchase or service use, and convert the potential price or loyalty/incentive value into an actual sale or use, with incentive or loyalty point capture; (5) capture the value of the Loyalty Application based transaction for future incentive or loyalty point calculation and use; (6) capture the transaction details in a database for future account activity analysis and actual purchase or procurement incentives assessment; and (7) utilize Loyalty Application specialized functionality, such as with health and educational services, so as to complete a transaction paid for by prior incentive value accumulation, or via monetization to provide a charitable donation.

Figure 8A:
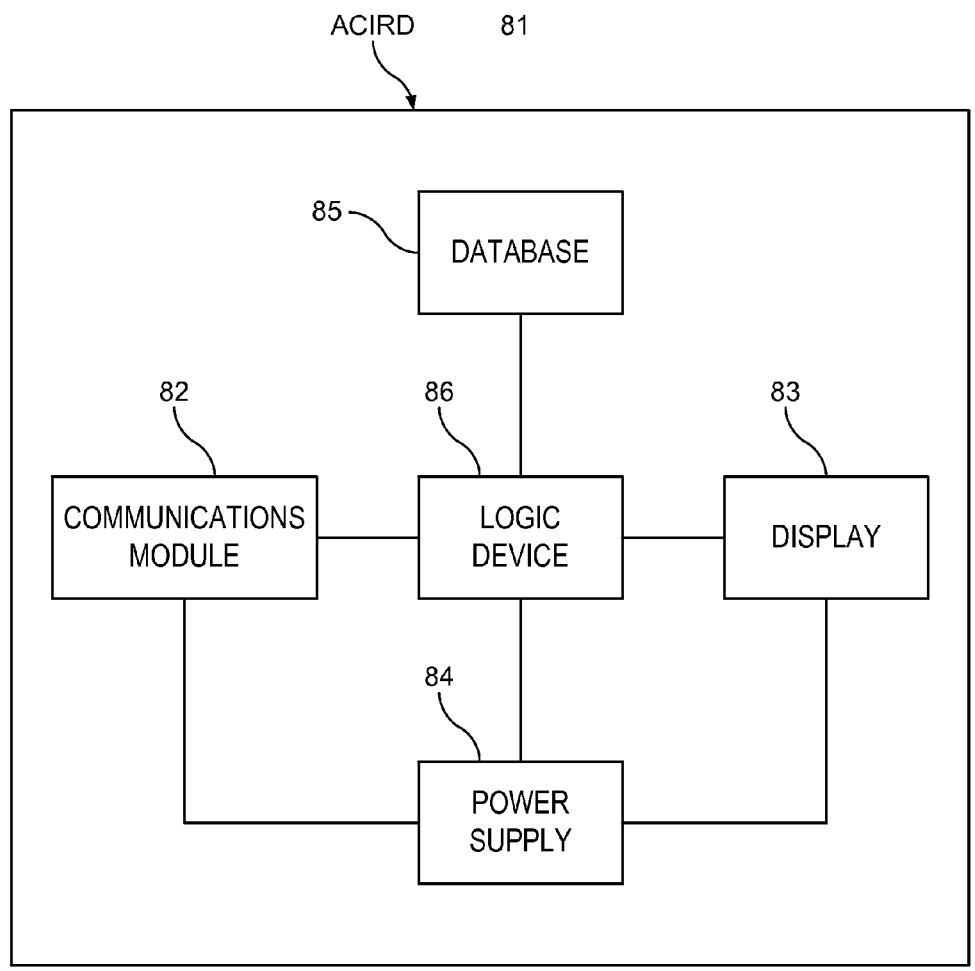

The product requirements for a Loyalty Application are illustrated in FIG. 8A. In addition to conventional SSD 104 system components as described herein, the Loyalty Application embodiments of the present invention comprise new stand-alone, programmable ACI Response Device (ACIRD) 81 with communications 82 and display 83 functionality. Device 81 is used at each purchase or service nexus to respond to the Smart Device 102/SSD 104 action. An ACIRD 81 can be reset or interrogated remotely by a central control system, such as an ACI 101.

The ACIRD 81 provides a remote and interim substitute for ACI 101 functions. Examples of its use are these:

1. A local (to SD 102/SSD 104) inquiry device with access to pre-stored data, such as a supermarket shelf product identification device or compilation of gymnasium incentive point values for specified exercise levels.
2. A controlled/secured entry to ACIRD 81 content to observe, upload, download, or change the ACIRD 81 content.
3. Initiation of an ACIRD 81 action as a prelude to requiring secure ACI 101 access for a controlled/confidential transaction.

The operation of the ACIRD 81 and SSD 104 in a Loyalty Application will now be described with respect to FIGS. 8A through 8D.

ACIRD 81 is a self-contained unit with its own power supply 84, logic device 86, database 85, communications module 82, and display 83. Device 81 accepts the following types of input messages: 1) An inquiry. This message activates a prepared display 83 message. The message can include a description of the item or service connected with the device 81 operation. 2) An order. This message allows the user to specify the quantity of product or service requested. 3) A change message, which allows ACIRD 81 to change the unit content and responses. 4) A remote inquiry message, requesting that activity content stored within ACIRD 81 is forwarded to the ACI 101 for record processing, inventory control, and/or preparation of summaries of services delivered.

For security purposes, ACIRD 81 has a content equivalent to that provided by an SSD 104, and includes said content with data being transferred to the ACI 101. This allows the ACI 101 to securely assess its input from a variety of SSD 104 and ACIRD 81 sources. There can be one SSD 104 for multiple ACIRDs 81.

Device 81 is usually physically located in or near the storage area for the cognizant product or service. As non-limiting examples, the ACIRD 81 can be integral to an admission acceptance or service location; integral to a manufacturing or fabrication location; integral to a direction setting location for a transportation or physical conveyance location; integrated into a communications originating location, a set top box, a smart device, a smart TV, etc.; or located at an educational or health services location, a sports event, or an entertainment venue.

FIG. 8B1 shows local operation or inquiry of an ACIRD 81 where an SSD 104 is not required for the transaction. As non-limiting examples, these are transactions where transaction data is being captured for future assessment or use, or monetization or redistribution to family members or charitable causes.

In FIG. 8B1, SD 102 initiates a transaction at step 810. At step 811, ACIRD 81 receives the transaction request, and, at step 812, accesses an appropriate database. At step 813, ACIRD 81 displays the results of the access on its display 83. At step 814, ACIRD 81 performs the transaction, in this case a redistribution of funds, and confirms the transfer to SD 102. At step 815, SD 102 displays the results of the transfer on its display. At step 816, the process ends.

FIG. 8B2 shows an example where ACIRD 81 is a particular species, namely an ATM (Automated Teller Machine) 91. At step 820, ATM 91 initiates a transaction and sends the request to SSD 104. At step 821, SSD 104 receives the requested transaction. At step 822, SSD 104 illuminates its indicator 116, or otherwise notifies its user that a transaction request is pending. At step 823, the user acknowledges the transaction request by means of actuating button or sensor 110 as previously described, or by any other means. At step 824, the processor 114 within SSD 104 enables the transaction to take place, and at step 825, the communications module 118 within SSD 104 instructs ATM 91 to process the transaction. In this example, the transaction comprises authorizing ATM 91 to dispense cash to the user of ATM 91.

At step 826, logic device 86 within ATM 91 checks to see whether the transaction may take place. In this case, for example, ATM 91 checks its store of cash to see whether enough cash is available to dispense, and checks to see whether the user of ATM 91 is authorized to receive that amount of cash on that particular day. If these verification steps are not completed successfully, the process ends at step 827 with no cash being dispensed. If, on the other hand, the verification steps do succeed, the cash is dispensed to the user at step 828. Then ATM 91 updates its database at step 829, and displays on its display 83 at step 830 a message to the user that the cash is being dispensed. The process ends at step 831.

While FIG. 8B2 has been described in terms of ACIRD 81 being an ATM 91, the method just described can be used where ACIRD 81 is a ticket dispenser for any activity requiring a ticket, such as a ride on public transportation, a theater event, a sporting event, etc. Similarly, ACIRD 81 can be a repository of loyalty information. In this embodiment, the transaction can involve the distribution of loyalty coupons to the user, and corresponding update of database 85.

FIG. 8B3 illustrates an embodiment of the present invention in which the database 85 of ACIRD 81 is updated, changed, or unloaded. In this embodiment, ACIRD 81 initiates the transaction at step 840, and sends a transaction request to SSD 104. At step 841, SSD 104 receives the transaction request, and, at step 842, SSD 104 signals its user, by any of the means previously described (such as by illuminating indicator 116) that a request has been received. When the user authorizes the transaction, he or she actuates button/sensor 110, or uses any other technique, to notify SSD 104, at step 843. At step 844, SSD 104 enables and processes the transaction request, utilizing its processor 114. At step 845, SSD 104 communicates the transaction to ACIRD 81 via its communications module 118. At step 846, ACIRD 81 receives this transaction message and accesses appropriate areas within its database 85. At step 847, ACIRD 81 implements the cognizant transfer or change using its logic device 86. At step 848, ACIRD 81 displays the transaction on its display 83. The method ends at step 849.

Figure 8C:
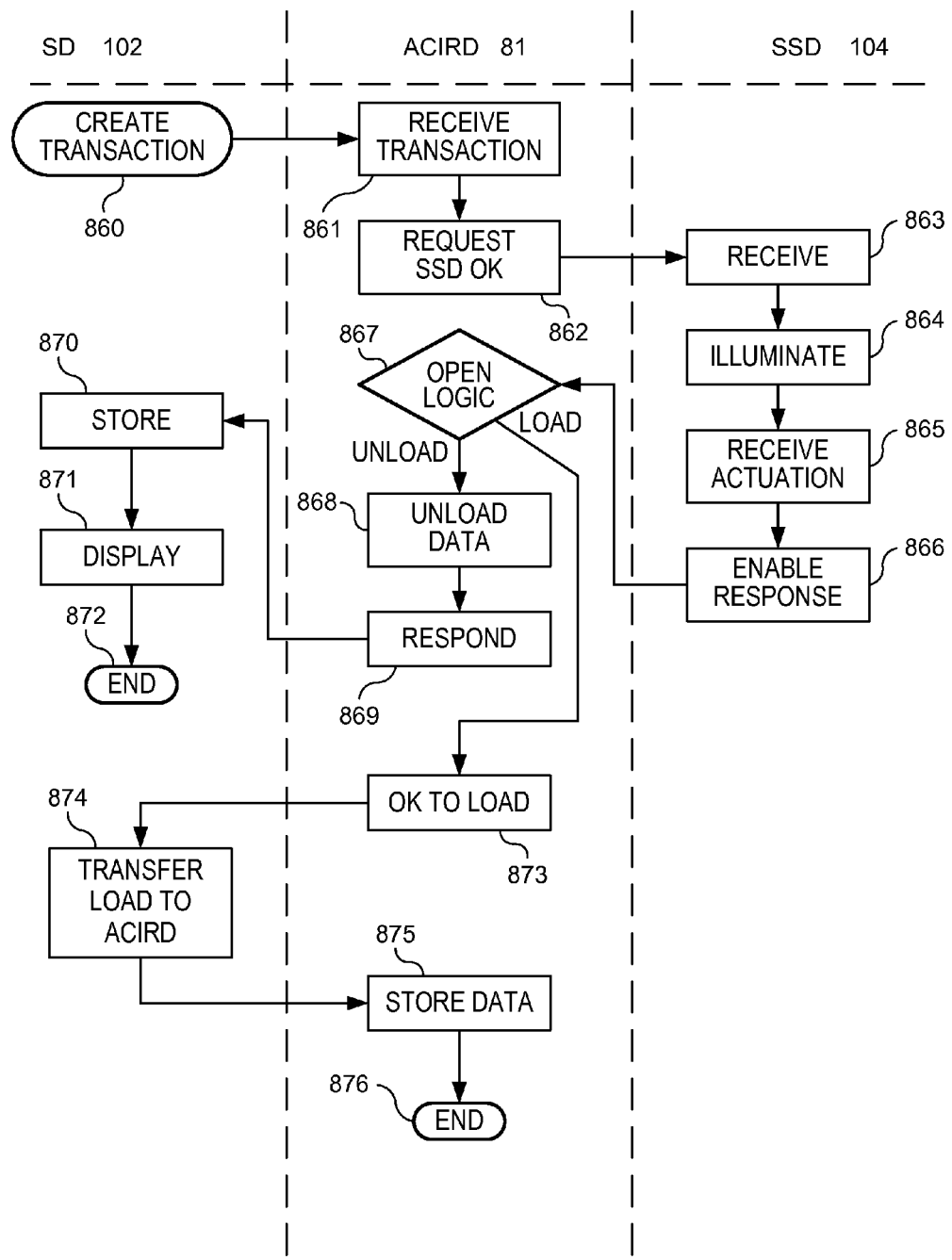

FIG. 8C illustrates confidential load and unload of ACIRD 81 data locally. In this context, "locally" means without needing to communicate with an ACI 101. The method includes, e.g., ACIRD 81 accumulating the device or service value of multiple purchases or service actions to determine accumulated incentive value and position.

At step 860, SD 102 creates a transaction request and sends it to ACIRD 81. At step 861, ACIRD 81 receives the transaction request. At step 862, ACIRD 81 checks the SSD unit identifier that was given to it with the transaction request, and forwards the transaction request to SSD 104. At step 863, SSD 104 receives the transaction request, and, at step 864, notifies its user (by any of the means previously discussed, such as by activation of indicator 116) that a transaction request is pending. Assuming that the user desires to go ahead with the transaction, SSD 104 receives actuation from the user at step 865 via any of the means previously discussed, such as the user activating button/sensor 110. At step 866, SSD 104 authorizes and processes the transaction using its processor 114, and conveys this fact to ACIRD 81 via its communications module 118.

At step 867, ACIRD 81 opens logic within its logic device 86 to decode the transaction. If the transaction is to unload data from ACIRD 81 to SD 102, ACIRD 81 prepares instructions to accomplish this at step 868 and, at step 869, so notifies SD 102. At step 870, SD 102 stores the data it has just received from ACIRD 81 and, at step 871, displays a message to its user. The process then ends at step 872.

If, on the other hand, the transaction is to load data from SD 102 to ACIRD 81, at step 873, ACIRD 81 prepares instructions to accomplish this and sends the instructions to SD 102. At step 874, SD 102 then prepares the necessary data package and transfer instructions, and sends this to ACIRD 81. At step 875, ACIRD 81 then stores the data it has just received from SD 102. The process then ends at step 876.

Figure 8D:
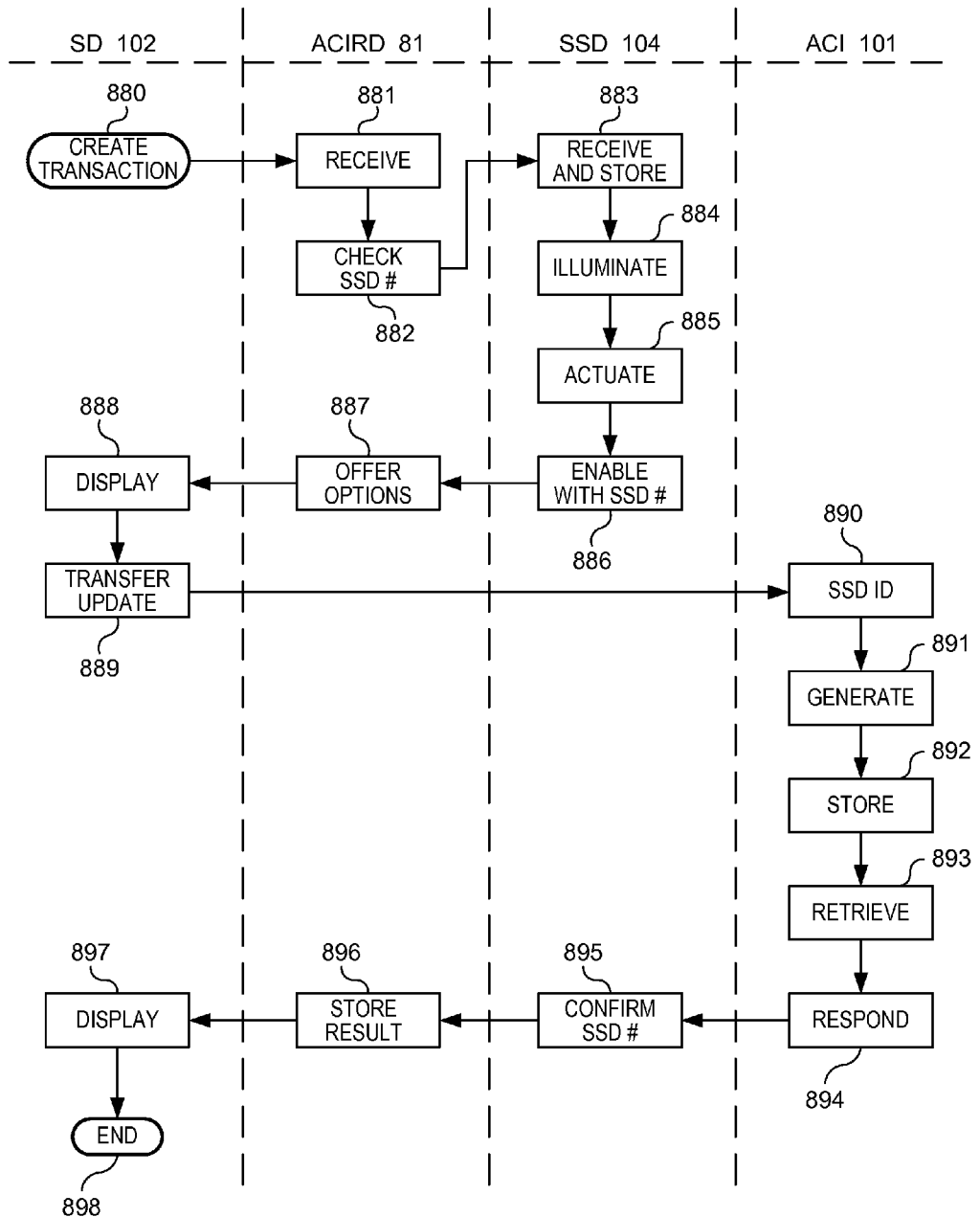

FIG. 8D illustrates the confidential exchange of ACIRD 81 data with ACI 101 data. In this method, selected data accumulated over time within ACIRD 81 is forwarded to the account based ACI 101, and stored there as identified in the transaction captured data. The ACIRD 81 is used as a buffer and a data aggregator to avoid overwhelming the ACI 101 with a mass of individual transactions and their detailed data. From the perspective of time, ACIRD 81 acts as an interim data capture facilitating device. As before, ACI 101 provides stored, retrieved, and generated data. Note that the method described in FIG. 8D occurs, at least in part, online, because an ACI 101 is involved. Thus, it is not considered to be a "local" method.

At step 880, SD 102 creates a transaction request and sends it to ACIRD 81. At step 881, ACIRD 81 receives the transaction request, and at step 882 checks the SSD unit identifier that was given along with the transaction request. If the SSD unit identifier checks out, ACIRD 81 forwards the transaction request to SSD 104, which receives it at step 883 and stores it within its memory 112.

At step 884, SSD 104 sends a message to its user by any of the means previously described, such as by illuminating indicator 116, that a transaction request is pending. Assuming that the user wishes the transaction to proceed, the user actuates button/sensor 110, or notifies SSD 104 by any other means, at step 885. At step 886, SSD 104 uses its processor 114 to enable and process the transaction, and so notifies ACIRD 81 in a message that includes the unit identifier for SSD 104 as a security precaution. At step 887, ACIRD 81 processes the message and considers appropriate options that it may offer to the user of SD 102, and forwards this message to SD 102. These options can include, for example, offers to redeem loyalty points at participating merchants, or incentives to participate in a corporate wellness program. At step 888, SD 102 displays the message on its display. At step 889, SD 102 then authorizes the data transfer and sends the transfer message to ACI 101 using the SSD ID as an index. At step 890, ACI 101 verifies the validity of the SSD ID. At step 891, ACI 101 generates appropriate housekeeping and storage commands. At step 892, ACIRD 81 stores the data in its database.

The remaining steps in FIG. 8D are optional. At step 893, ACI 101 retrieves selected information from its database and, at step 894, sends a confirmatory response containing the SSD unit identifier to SSD 104. At step 895, SSD 104 confirms the validity of the SSD unit identifier, and forwards the confirmatory message to ACIRD 81. At step 896, ACIRD 81 updates its database with this confirmation and forwards the confirmation to SD 102. At step 897, SD 102 puts a confirmation message on its display so as to notify its user that the transaction has been successfully completed. At step 898, the method ends.

Example of ACIRD 81 Use

As an example of an ACIRD 81-based transaction sample, consider a purchase environment such as purchase of a supermarket shelf item. The user brings his or her Smart Device 102 into the communications required range of the shelf item. An application within SD 102 transmits a signal to the user's SPARC Security Device 104. The SSD 104 executes the following sequence of events: 1) it interrogates ACIRD 81 (which can be physically located on the supermarket shelf) to receive a description of the shelf item, its cost, and transaction loyalty value; 2) it exercises a purchase action, supported by the SD 102; 3) it transmits the purchase transaction to the ACI 101 associated with that application, including the loyalty value of the transaction; and 4) it initiates a value transaction to the ACIRD 81, where the value transactions for a preset period are accumulated for that user for later transfer to the ACI 101. The application within SD 102 can use the value for deciding whether subsequent purchases are worth making, and for generating reports of the user's purchases.

Summary of ACIRD 81 Use

In summary, the ACI 101 processes the user's account based monetary data and/or other transactions, after assuring correct security content of the transaction messages. The ACIRD 81 processes the incentive, loyalty, or quantity related value data and transactions, again using a security identification. The content of the value data includes a broad spectrum of value factors that are selected and set by the users and participating entities prior to inclusion in the process. As in the non-ACIRD embodiments described herein, the SSD 104 provides a vital control function which prevents Smart Device 102 misuse when the device 102 is lost or stolen. As described previously, SSD 104 prevents use of overheard transmission to steal vital transaction or identification data, provides a means to prevent downloading fraudulent applications, and allows loyalty incentive monetization programs.

Unsolicited Transactions (UTs)

Up to now, we have discussed the security of a transaction originating on a Smart Device 102, and the response to this origination from an Application Controlling Institution (ACI) 101. Now, with reference to FIGS. 9 and 10, we will discuss security issues arising from transactions originating from an entity 906 other than a Smart Device 102. These transactions are unsolicited from the point of view of the destination Smart Device 102, and can originate from one or more external sources 906, such as the Internet or other communications networks. We refer to these transactions as Unsolicited Transactions (UT's). The nature of these transactions can be anything previously described in this patent application. For example, the source 906 may be a bank wishing to communicate with its customer 102.

Figure 9:
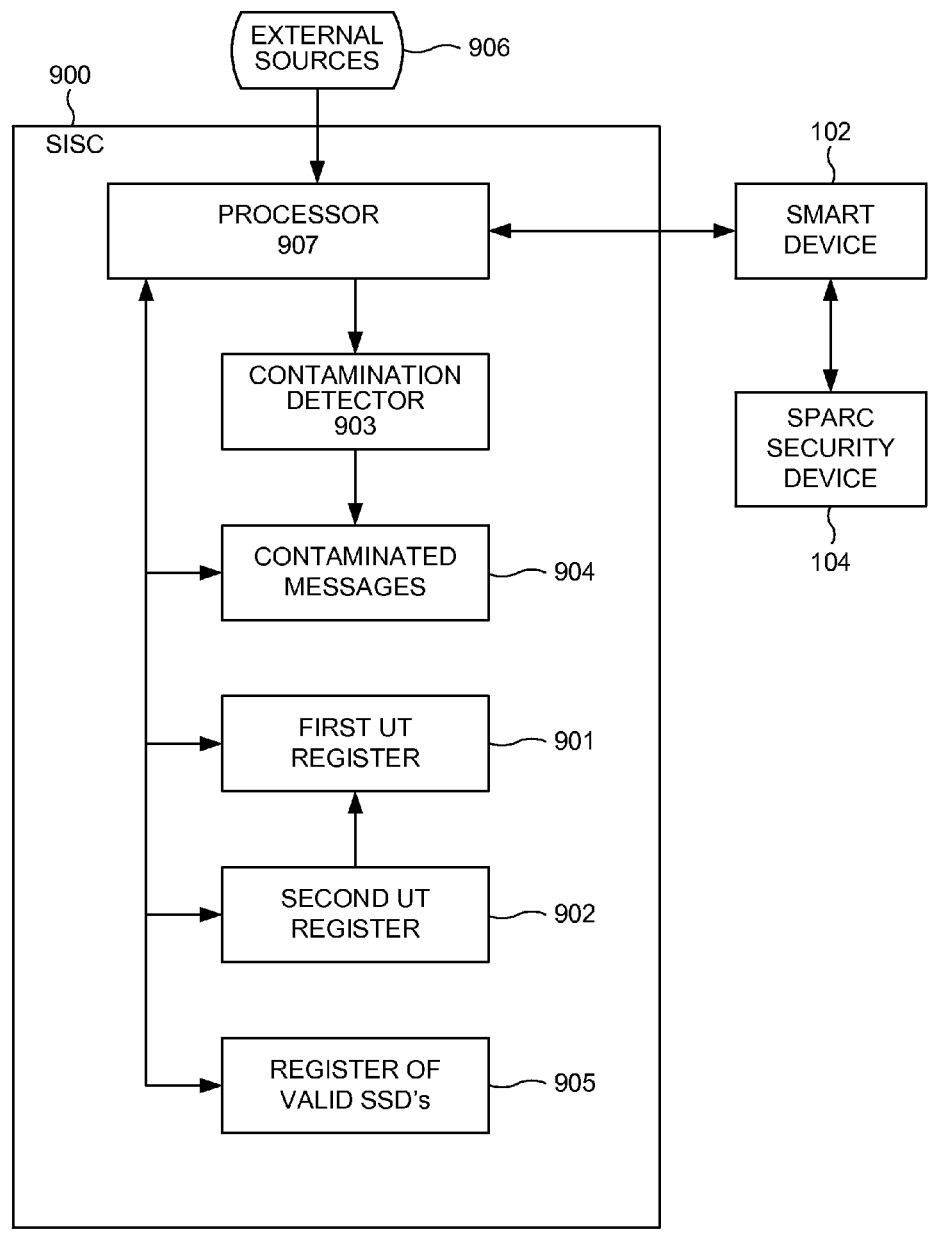
FIG. 9 is a block diagram of an embodiment of the present invention in which Smart Device 102 receives a request for an unsolicited transaction (UT) from an external source 906.

This UT security issue is addressed by the introduction of two (typically 40 digit long) UT registers 901, 902. The first UT register 901 contains a validity identifier used to identify validly screened content that has been originated by an external communication source 906 and has been addressed to a Smart Device 102 that has subscribed to the UT service. The second UT register 902 contains a similar validity identifier that is used to re-synchronize the validly screened content if and when the message flow is interrupted for any reason. FIG. 9 shows registers 901, 902 being associated within SISC 900 (which is described below), but these registers 901, 902 can also be contained within a participating SSD 104.

1. Scanning Communications Sources 906 for Valid Content

Figure 10:
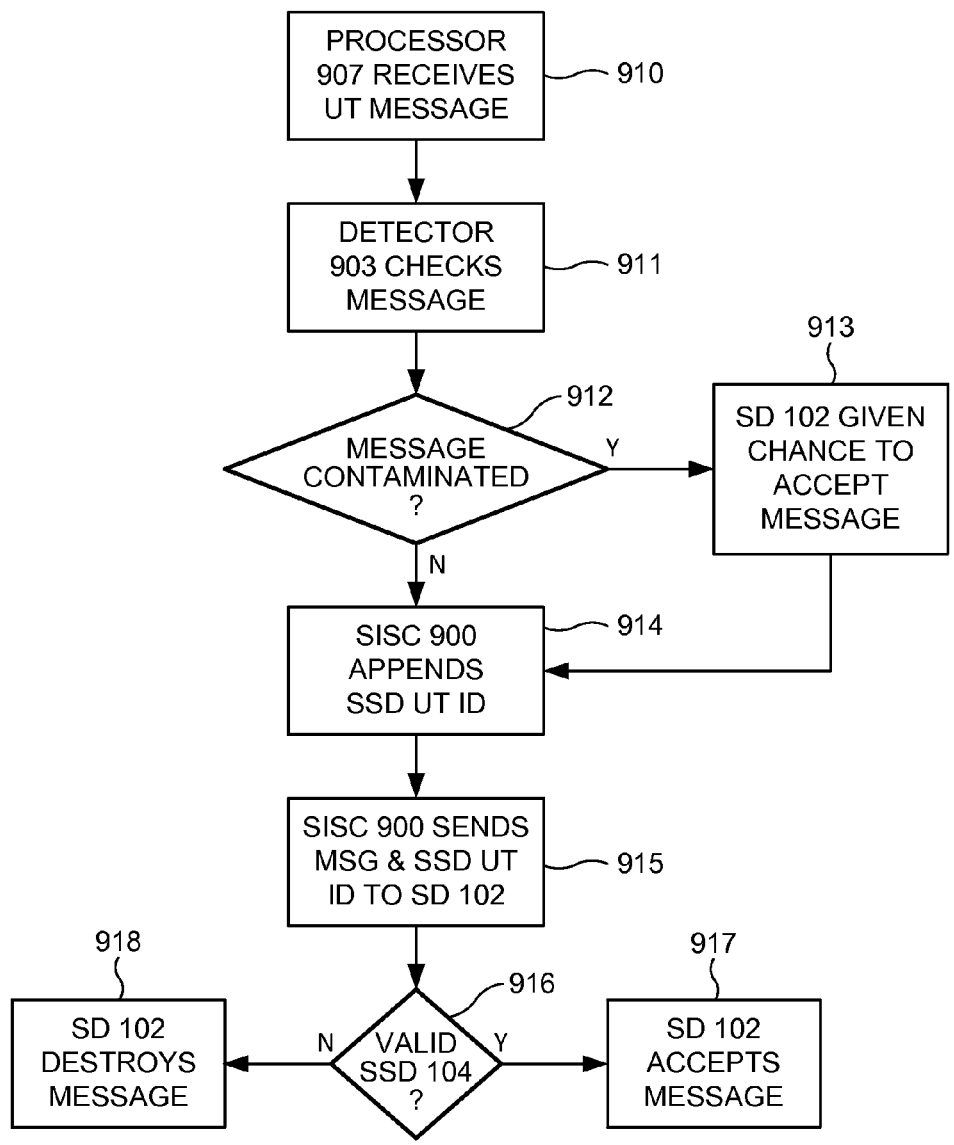
FIG. 10 is a flow diagram of a method embodiment of the present invention corresponding to the apparatus depicted in FIG. 9.

A service entity 900, which we call here the SPARC Internet Security Corporation (SISC), contains a processor 907 that scans or otherwise receives externally-originated incoming messages that are addressed to the e-mail address of a participating Smart Device 102 (step 910 in FIG. 10). A "participating Smart Device 102" is one whose user has contractually enrolled in the UT service. Processor 907 directs each incoming message through a Contamination Detector 903 (step 911), which determines whether the incoming message contains the identical validity identifier that is stored in the first UT register 901 (step 912). A message that contains this validity identifier 901 is deemed to be a valid message or an "uncontaminated message". A message that does not contain the validity identifier stored in the first UT register 901 is deemed to be "contaminated". The validity identifier 901 can be any combination of numbers, letters, and/or other characters, such as ASCII characters.

For contaminated messages, processor 907 preferably generates a notice to the intended recipient Smart Device 102. The notice informs the user of the recipient Smart Device 102 of his/her option to ask that the message be sent to the Smart Device 102 despite its having been declared to be "contaminated" (step 913). Contaminated messages are stored in a register 904 within SISC 900 for a preselected period (waiting time) pending the recipient's 102 reply. If a request to forward the contaminated message to the Smart Device 102 is not received by SISC 900 from the SD 102 within the specified waiting period, processor 907 destroys the contaminated message.

2. Preparing Uncontaminated Content for Communication to Smart Device 102

SISC 900 maintains a register 905 of valid SSD 104 addresses, i.e., addresses of SSD 104's that are pre-authorized to participate in the UT scheme. Each uncontaminated message contains the e-mail address of the recipient Smart Device 102. Processor 907 adds an SSD UT Identifier to the message, signifying that the message has been determined by Contamination Detector 903 to be uncontaminated (step 914). The SSD UT Identifier comprises the address (or other unique identifier) of the SSD 104 that has been pre-authorized to participate in this UT scheme by SD 102, and an optional message count. The message count facilitates detection of any overheard transmission being illegally reused. This illegal reuse can be detected by processor 907 observing that two incoming messages have the same message count. The message count is added to the SSD UT Identifier by processor 907, and is a count of the number of valid messages that have been sent to the particular Smart Device 102, regardless of the source 906. Processor 907 changes the count from message to message by applying an algorithm. The algorithm does not simply increment the count by 1 from one message to the next, as doing so would make it easier for nefarious persons to break into the system.

Processor 907 then sends the UT message with the appended SSD UT Identifier to SD 102 (step 915).

3. Receipt of a Message with SSD UT Identifier at the Smart Device 102

There are four types of messages that can arrive at the Smart Device 102.

1) Transactions that originated at the Smart Device 102 and have been returned to the Smart Device 102 by an ACI 101 with a validated SSD ID, as discussed above in conjunction with previously-described embodiments of this invention.

2) A UT message successfully cleared by SISC 900, with the SSD UT Identifier appended. For such a message, Smart Device 102 checks the unique SSD 104 identifier portion of the SSD UT Identifier against its internal database (step 916), and, when SD 102 determines that the unique SSD 104 identifier is valid, processes the incoming message as a valid message (step 917).

3) A UT message without a valid SSD UT Identifier, such as a SSD UT Identifier having a missing or invalid unique SSD 104 identifier. Smart Device 102 summarily destroys such messages as being too risky for further consideration (step 918).

4) Transaction content received from another Smart Device 102, such as in a bumping action. As used herein, a "bumping action" is a communication between two Smart Devices 102 that are proximate to each other, e.g., within NFC range, and that share a bumping application program. In this case, the recipient Smart Device 102 accepts or rejects the content based upon the dictates of the shared bumping application program.

4. Interruption of Message Flow

If the incoming UT message flow is interrupted for any reason, such as a break in the communications link between the source 906 and SISC 900, processor 907 moves the contents of the second UT register 902 into the first UT register 901, to re-synchronize the process. Then processor 907 inserts a new validity identifier into the second UT register 902, and securely conveys the new validity identifier 902 to sources 906 that have been authorized to participate in the UT system. The new validity identifier 902 must be different than the first validity identifier 901, and can be generated by a random number generator or a random character generator, for example.

In another embodiment of the invention, all Smart Devices 102 are designed with the ability to have just Near Field Communications (NFC) or other short-range communication capability, i.e., the Smart Devices 102 are disabled from communicating with wide area networks 506, such as the Internet or other external networks. In this embodiment, Smart Device 102 is able to communicate only with its corresponding SPARC Security Devices 104. The user of a Smart Device 102 who wishes to engage in communications with the external network 506 must conduct such communications through its corresponding SSD 104.

Major advantages of this embodiment accrue from the fact that all security functions and concerns are removed from Smart Device 102. Smart Device 102 is thereby able to run all software applications in their standard form, without having to purchase, install, or run security enhanced versions of the software applications, and without having to modify existing software applications. This embodiment is particularly useful for senior citizens or others who are prone to lose or misuse their Smart Devices 102. This embodiment speeds SD 102 transactions, in that for outgoing (outgoing from the point of view of SD 102) messages, there is no need for acknowledgement messages to be sent back to the SD 102. For incoming messages to the SSD 104, unacceptable messages are screened out before reaching the SD 102. The cost of operating the SD 102 is lowered, because the SD 102 does not need to communicate with the Internet or other external network 506, eliminating any need for PINs, passwords, and/or encryption to protect such network 506 transmissions.

In this embodiment, when SD 102 wishes to send a message via external network 506, SD 102 first composes the message and sends it to its associated SSD 104. The human user of SSD 104 is alerted (e.g., via indicator 116) that an outgoing message has been presented to SSD 104, and must affirmatively take some action, such as by pressing button 110, before the message is released and relayed to external network 506. Similarly, an incoming message from external network 506 to SD 102 is first routed through the matching SSD 104, where again the human user of SSD 104 is alerted, e.g., via indicator 116. The user of SSD 104 then must take affirmative action, such as by pressing button 110, before the message is released and relayed to SD 102.

Control of Remote Devices

Figure 11:
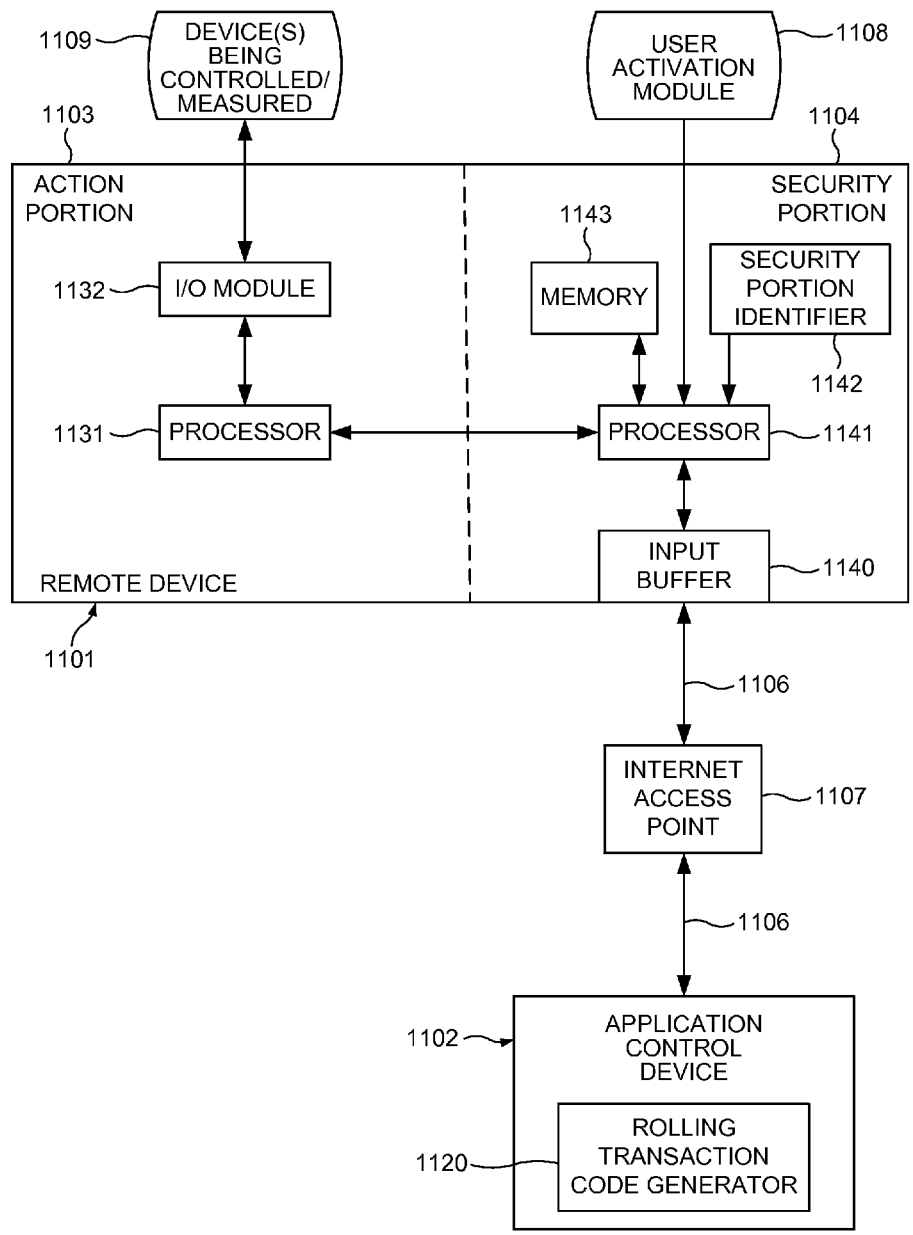
FIG. 11 is a block diagram of an embodiment of the present invention in which a remote device 1101 is controlled.

The principles of the SPARC security solution that have been described above can be extended to control of remote devices 1101, as shown in FIG. 11. In this series of embodiments, Remote Device 1101 is analogous to Application Controlling Institution 101 as heretofore described, Application Control Device 1102 is analogous to Smart Device 102 as heretofore described, and Security Portion 1104 is analogous to SPARC Security Device 104 as heretofore described. One difference in this series of embodiments is that a rolling transaction code, which is analogous to the one-time transaction number heretofore described, is generated by Application Control Device 1102 rather than by Security Portion 1104.

As shown in FIG. 11, Remote Device 1101 comprises two portions, Action Portion 1103 and Security Portion 1104.

Action Portion 1103 controls and/or measures one or more Devices 1109. Examples of Device parameters that can be controlled by Action Portion 1103 include, but are not limited to, temperature in a room or building, air flow in a room or building, lighting in a room or building, and operation of a burglar alarm. Action Portion 1103 can be instructed by Application Control Device 1102 to control one or more than one Device 1109, simultaneously or seriatim. Alternatively, Action Portion 1103 can relay to Application Control Device 1102 measurements from the Device(s) 1109 being measured. Examples of Device sensors that can be measured by Action Portion 1103 include, but are not limited to, a thermometer, a relative humidity gauge, an air flow monitor, a camera (which can be a still camera or a video camera), and an altimeter.

Action Portion 1103 typically comprises an input/output module 1132 for communicating with the Device(s) 1109, and a processor 1131 coupled to input/output module 1132 and to processor 1141.

Application Control Device 1102 is situated remotely from Remote Device 1101, and communicates with Remote Device 1101 via an electronic connection 1106. Electronic connection 1106 may comprise the Internet, in which case one or more Internet Access Points (routers) 1107 are coupled between Remote Device 1101 and Application Control Device 1102.

A long felt but unmet need in the remote control industry has been adequate security protection for the operation of such remote devices. The security problems have fallen into three general categories:

1. The remote devices can be stolen, or damaged in a natural catastrophe.
2. Communications between the remote device and its remote application control point are subject to being intercepted by nefarious entities.
3. Nefarious entities have been able to download malware into such remote devices, which has led to catastrophic results when the remote devices have been used in the operation of critical infrastructure, such as nuclear power plants.

The present invention elegantly and simply satisfies these long felt but unmet needs.

In the present invention, Security Portion 1104 is added to Action Portion 1103 of Remote Device 1101. Security Portion 1104 comprises a read-only memory 1142 containing a unique security portion identifier, which, as alluded to previously, is analogous to the unique SSD 104 unit identifier referred to previously in this specification. Security Portion 1104 also typically comprises a processor 1141 and an input buffer 1140, which buffers outgoing and incoming messages/data that are sent to and received from Application Control Device 1102.

Another aspect of this invention is a rolling transaction code generator 1120 that is associated with (e.g., contained within) Application Control Device 1102. As stated previously, this rolling transaction code is analogous to the one-time transaction number previously described in this specification. The rolling transaction code typically comprises the current date, the current time, a unique identification of the Remote Device 1101 being controlled, and an optional field, which may include relevant comments, subject matter information, etc. This rolling transaction code follows the principle of de-identification, which means that no user account numbers are used. This greatly contributes to the overall security of the system. In lieu of a user account number, the rolling transaction code also comprises a unique occurrence number, which uniquely identifies the particular transaction (occurrence), i.e., a number that identifies which particular occurrence of control or measurement is being exercised. This occurrence number (which can contain elements other than numbers, such as letters, punctuation marks, etc.) is changed for each such occurrence. For reasons of security, the occurrence number should not be simply incremented for each occurrence, because that would make it easier for nefarious entities to hack the system.

In operation, processor 1141 checks the rolling transaction code against pre-stored information contained in a random access memory 1143 associated with processor 1141, and verifies the validity of the rolling transaction code before allowing the transaction to proceed. As another security feature, processor 1141 also checks that each control message sent from Application Control Device 1102 to Security Portion 1104 contains the correct security portion identifier 1142 for that particular Security Portion 1104. Of course, it is important to maintain the confidentiality of security portion identifier 1142.

Processor 1141 also checks to see that there is a valid connection from processor 1131 before processor 1141 forwards commands to processor 1131. This guards against the first security issue identified above, namely, the eventuality that Remote Device 1101 has become disabled.

As another means to improve the security of the system, a User Activation Module 1108, separate and apart from Application Control Device 102, can be associated with (either proximally or distally) Security Portion 1104. In these embodiments, User Activation Module 1108 accepts one or more of a set of pre-established identification/verification inputs before processor 1141, which is coupled to User Activation Module 1108, is allowed to perform any of its designated tasks. Such identification/verification inputs can include, but are not limited to, biometric inputs (such as fingerprints and retinal scans), alphanumeric inputs such as a PIN (Personal Identification Number), and/or physical keys.

SPARCPrivate and SPARCeiver

Figure 12:
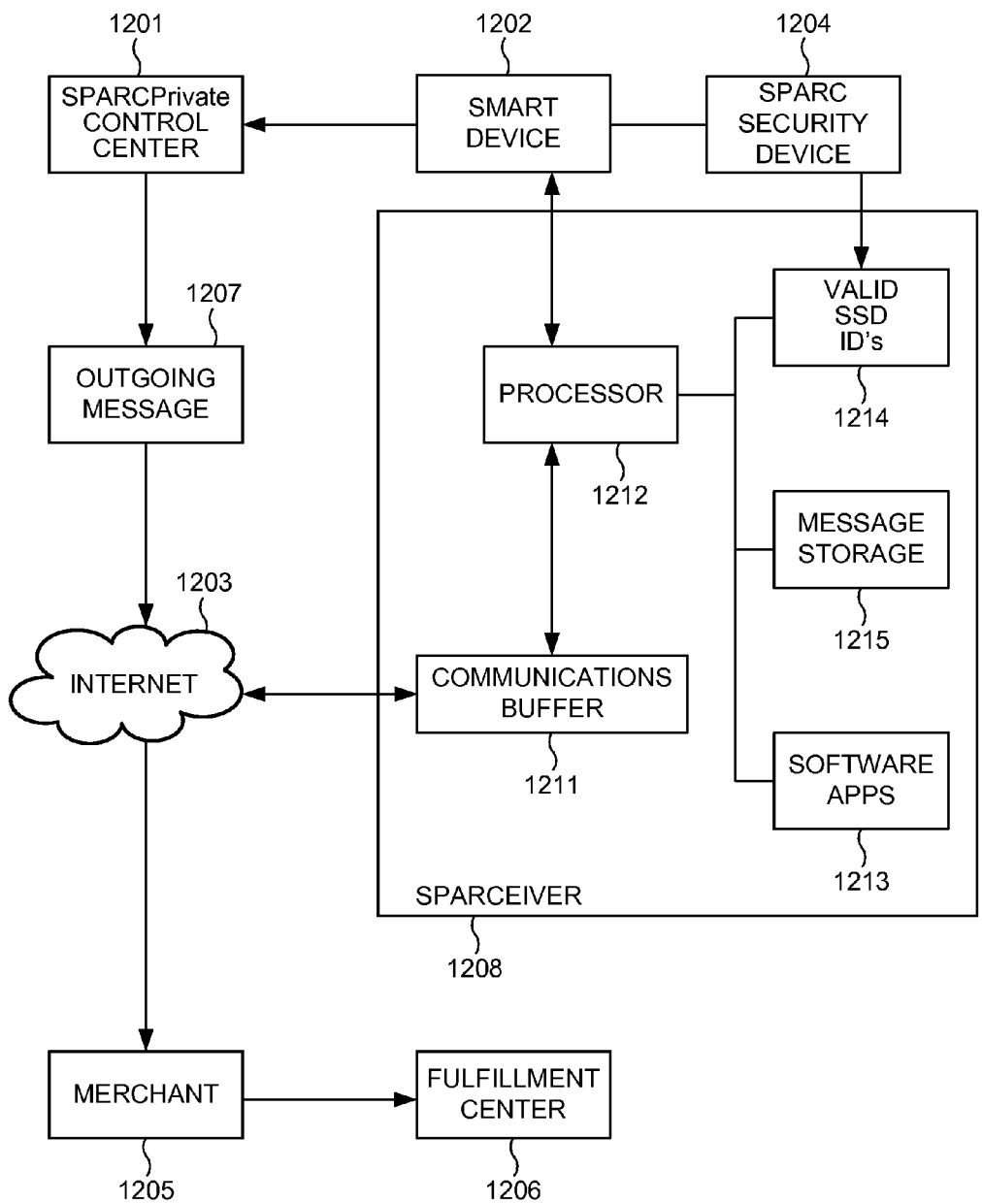
FIG. 12 is a block diagram of an embodiment of the present invention in which SPARCeiver 1208 is employed.

The principles described herein can be further extended to a system which we here characterize as SPARCPrivate. With reference to FIG. 12, users of Smart Devices 1202 (such as those described previously in this specification) face two major security threats when sending and receiving messages over an open network such as the Internet 1203.

The first major security threat is that outgoing (from the point of view of Smart Device 1202) messages could be read (intercepted) by third parties for purposes of invading the privacy of the sending Smart Device 1202. This nefarious activity can include capturing the identification of the Smart Device 1202 and/or spying on the actions of the Smart Device 1202.

The second major security threat is that incoming (into Smart Device 1202) messages could contain one or more of a wide variety of viruses, fraudulent software applications, and/or other types of malware. All of this malware is designed to injure the message recipient 1202 and/or to steal the identification and/or personal information of the recipient 1202.

The present invention addresses these security threats in the following manner. A SPARCPrivate Control Center 1201 is coupled to the Smart Device 1202, and is adapted to receive from the Smart Device a unique security device identification that the Smart Device 1202 has received from its associated SPARC Security Device 1204. Control Center 1201 also receives from Smart Device 102 a smart device identifier and instructions for initiating a transaction, such as a request to purchase a package from a merchant 1205. The SPARCPrivate Control Center 1201, which can be functionally identical to the Application Controlling Institution 101 described previously in this specification, checks the validity of the smart device identifier, and replaces the smart device identifier with the security device identification. This follows the principle of de-identification described previously herein, and hinders the ability of nefarious entities to spy on the actions of Smart Device 1202.

The SPARCPrivate Control Center 1201 includes the security device identification and the instructions in an outgoing message 1207, which Control Center 1201 then sends to the merchant 1205 over the the Internet 1203.

To further enhance security, SPARCPrivate Control Center 1201 in some embodiments adds two physical return addresses to the message 1207 before sending the message 1207 to the merchant 1205. The first physical address is that of the entity associated with the Smart Device 1202, i.e., the address where the user of the Smart Device 1202 wishes the package from the merchant 1205 to be sent. The second physical address is that of an intermediary fulfillment center 1206. In these embodiments, the merchant 1205 sends the package that has been ordered to the physical address of the fulfillment center 1206, along with the first physical address. The fulfillment center 1206, in turn, sends the package to the first physical address by usual delivery means, such as USPS, Federal Express, UPS, DHL, etc.

When implemented as a business, the user of the Smart Device 1202 wishing to use this SPARCPrivate service can be asked to pay a monthly fee and/or a fee per transaction and/or any additional freight charges necessitated by the package being sent via the fulfillment center 1206 (rather than being sent directly from the merchant 1205).

Other embodiments include another feature to increase security even further: the association of a security module that we refer to as SPARCeiver 1208 with the input side of the Smart Device 1202. In these embodiments, incoming messages that are sent to the Smart Device 1202 from the Internet 1203 must first pass through the SPARCeiver 1208, which performs a real-time malware scan to detect and remove from each message as many viruses, fraudulent software applications, and other types of malware before allowing the message to be forwarded to the Smart Device 1202. Optionally, SPARCeiver 1208 also replaces a security device identification that may be associated with the incoming message with the smart device identifier, which enables the Smart Device 1202 to check the smart device identifier in the incoming message with what the Smart Device 1202 knows to be its true smart device identifier, before Smart Device 102 accepts the incoming message.

SPARCeiver 1208 can be a stand-alone interface to the Internet 1203, and can be used in conjunction with any Smart Device 1202. Alternatively, SPARCeiver 1208 can be built into Smart Device 1202 and act as Device 102's interface to the Internet 1203. Each SPARCeiver 1208 has a companion SPARC Security Device 1204.

SPARCeiver 1208 typically has a physical size smaller than the size of a smart phone. SPARCeiver 1208 typically contains a communications buffer 1211, which receives and buffers incoming messages received from the Internet 1203, and formats and buffers outgoing messages prior to their being sent over the Internet 1203. Coupled to the communications buffer 1211 is a processor 1212, which contains programmable logic and arithmetic, and performs all of the functions that one normally attributes to a microprocessor. Processor 1212 is coupled to Smart Device 1202, and is also coupled to three memories (storage areas): a memory module 1213 that stores software applications that are used by the processor 1212, a memory module 1214 containing a set of valid security device identifications, and a memory module 1215 that serves as a temporary storage for messages that are being worked on by processor 1212. The companion SPARC Security Device 1204 is coupled to processor 1212 (e.g., indirectly via buffer 1211) via memory 1214. The coupling means is typically an NFC interface 1216. The three memories, 1213, 1214, and 1215, can be flash drives each having a capacity of about 3 Gigabytes.

The communications buffer 1211 typically has a storage capacity sufficient to buffer between 10 and 100 messages, based upon the model of SPARCeiver 1208 that is selected by the customer. The processing speed of processor 1212 can also vary based upon the model selected by the customer, and is typically roughly proportional to the size of communications buffer 1211.

In operation, SPARCeiver 1208 buffers all incoming messages arriving from the Internet 1203 using communications buffer 1211, and then processor 1212 scans each incoming message for malware. Processor 1212 does this by invoking anti-malware software that is stored in memory 1213. If the incoming message passes the malware test, processor 1212 temporarily stores the message in memory 1215. If the message fails the malware test, processor 1212 obliterates the message containing the malware.

Some, but not all, incoming messages contain a security device identification. The presence of a security device identification in the incoming message provides an additional level of security, compared to those incoming messages that do not contain a security device identification.

For those incoming messages that do contain a security device identification, processor 1212 checks the validity of the security device identification by means of consulting the memory 1214. If the security device identification is valid, processor 1212 moves the incoming message from temporary storage 1215 into Smart Device 1202, which processes the message. If the security device identification in the incoming message is invalid, processor 1212 obliterates the message.

For each outgoing message that is sent from Smart Device 1202 over the Internet 1203, the message is first sent to SPARCeiver 1208. Processor 1212 temporarily stores the message in memory 1215. Processor 1212 then invokes the anti-malware scanning software application from memory 1213 to scan the message for malware. If malware is present in the message, processor 1212 obliterates the message. If the message passes the malware test, processor 1212 affixes a valid security device identification to the message. Processor 1212 obtains this security device identification from memory 1214. Processor 1212 then sends the message to communications buffer 1211, which formats the message and sends it over the Internet 1203.

SPARChealth Security Device

Figure 13:
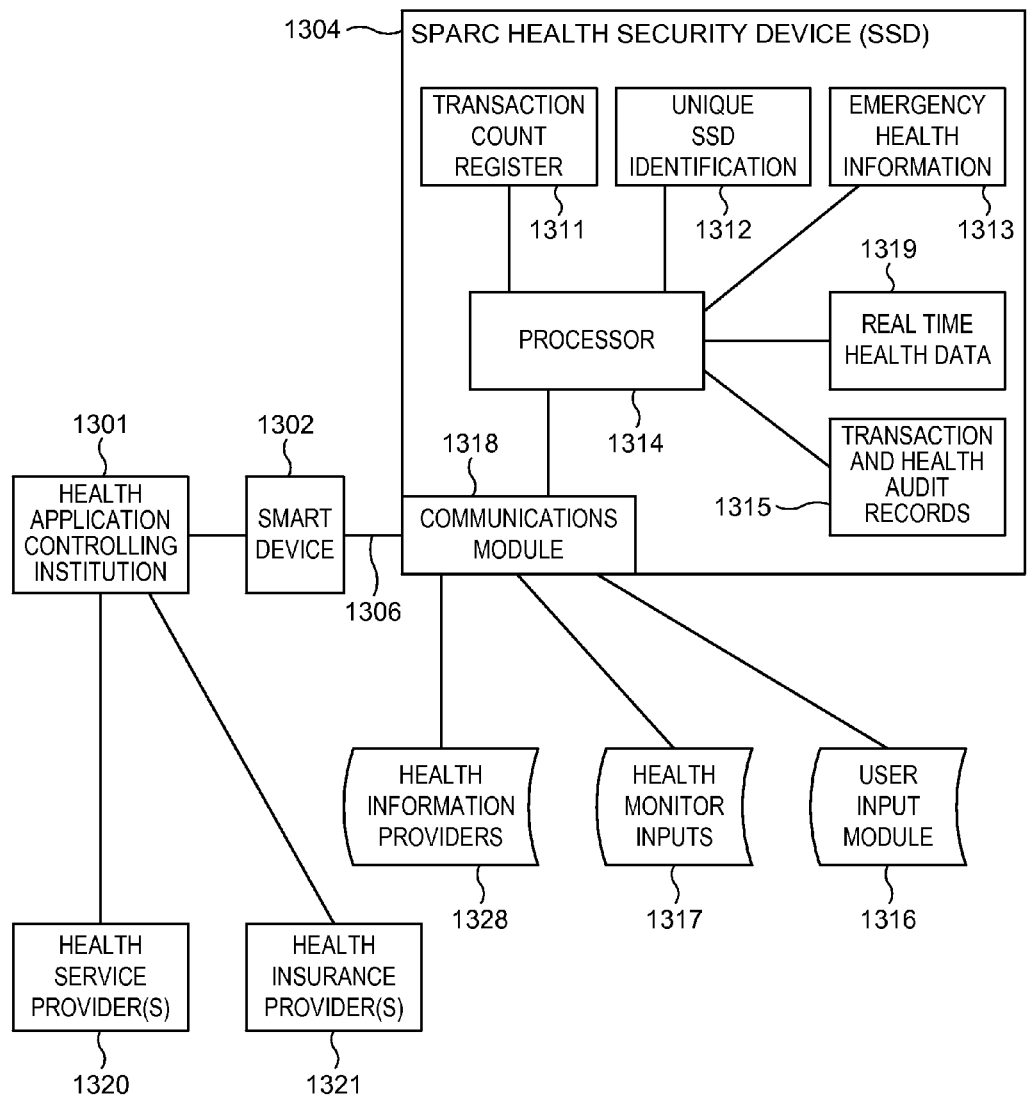
FIG. 13 is a block diagram of an embodiment of the present invention in which SPARChealth Security Device 1304 is employed.

In a further extension of the principles of the present invention as described previously herein, the SPARC Security Device 104 can be adapted to perform as a SPARChealth Security Device 1304, as illustrated in FIG. 13.

SPARChealth Security Device 1304 typically comprises a processor 1314 (analogous to processor 114 previously described), and, coupled to the processor 1314, a communications module 1318 (analogous to communications module 118) and a set of memory modules 1311, 1312, 1313, 1315, and 1319.

Processor 1314 contains programmable logic and arithmetic, as one would expect in a typical microprocessor.

One or more of memories 1311, 1312, 1313, 1315, 1319 can comprise a flash drive memory, e.g., one having about 3 Gigabytes of data capacity and the ability to connect to SPARChealth Security Device 1304 via a USB port associated with communications module 1318.

Memory 1311 is a rolling transaction count register, which stores the current transaction count for the particular health transaction that is being worked on by the SPARChealth Security Device 1304. Processor 1314 uses an algorithm to update the rolling transaction count for each current transaction, and stores this transaction count in register 1311. This updating is performed in the manner previously described in this specification, e.g., it is not wise from a security point of view to simply increment the transaction count by one for each subsequent transaction.

Memory 1312 stores a SPARChealth security device identification, which is unique for each SPARChealth Security Device 1304.

Memory 1313 stores emergency health information pertaining to the user of SPARChealth Security Device 1304. This emergency health information memory 1313, which can be thought of as a digital emergency card, typically stores emergency contact information for the user, the user's name, birth date, medication information, weight, eye color, blood type, organ donor status, physical address, and similar information.

Memory 1319 stores real time health information for the user. This information can be provided to SPARChealth Security Device 1304 via communications module 1318. This information can be provided by the user via user input module 1316, by one or more non-confidential health information providers (e.g., a provider who posted the information on a Web page) via module 1328, and/or by inputs from health monitor inputs module 1317, which serves as a vehicle for conveying to SSD 1304 measurements obtained by one or more health monitors, such as a heart monitor affixed to the user.

The real time health data memory 1319 stores information pertaining to, e.g., blood work, heart rate, hydration, blood pressure, typical physical activity level, nutrition, blood sugar level, amount of sleep that the user has enjoyed recently, respiratory rate, oxygen saturation, and the user's weight.

Memory 1315 serves as a place for processor 1314 to store historical information pertaining to transactions, such as records that are needed to comply with HIPAA legislation.

SPARChealth Security Device 1304 communicates with an accompanying Smart Device 1302 via a connection 1306, which is typically an NFC wireless connection. Smart Device 1302 is adapted to initiate health transactions originated by the user of SD 1302 and SSD 1304. These health transactions are initiated in the same manner as transactions that have been previously described in this specification. Confidential health transactions are communicated by Smart Device 1302 to a Health Application Controlling Institution (HACI) 1301, which can be structurally identical to the Application Controlling Institution 101 that has been previously described in this specification. When Smart Device 1302 communicates a transaction to HACI 1301, Smart Device 1302 forwards to HACI 1301 the unique SPARC security device identification 1312 and the rolling transaction count, but not any account information, credit card information, or other information that would identify the true user. This communication thus adheres to the principle of de-identification which has been previously discussed in this specification.

HACI 1301 processes the confidential health transaction by means of confidentially communicating with one or more health service providers 1320 and/or one or more health insurance providers 1321.

Similarly, when information is sent back from HACI 1301 to Smart Device 1302, the unique SPARChealth security device identification 1312 and the current transaction count are included with the return message, but not the user's account number, credit card information, or other information that could expose the true identity of the user.

Security for the Internet of Things

Figure 14:
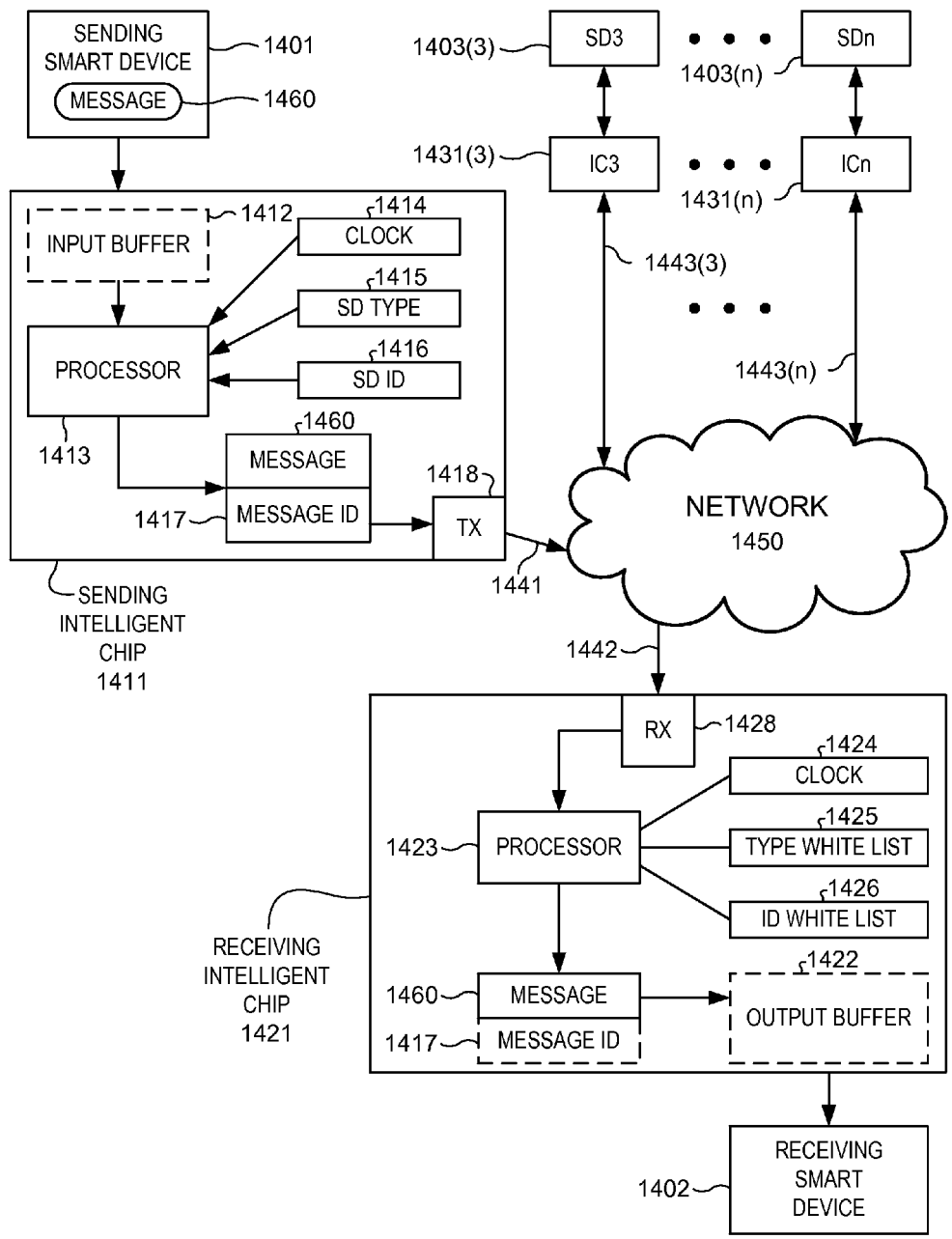
FIG. 14 is a block diagram illustrating a secure system for two or more smart devices 1401, 1402, 1403 to communicate with each other over a network 1450 without human intervention.

With reference to FIG. 14, a Network Of Things is a system wherein two or more smart devices 1401, 1402, 1403 communicate with each other over a network 1450 without human intervention. Network 1450 can be any wired or wireless communications network, such as a local area network (LAN) or wide area network (WAN), and is typically the Internet, in which case the Network Of Things is referred to as the Internet Of Things.

Peer-to-peer communications between and among non-human devices is becoming increasingly prevalent in modern society. For example, a food refrigerator may communicate with a supermarket to re-order food to restock itself. As another example, a household cooling fan may communicate with a room thermometer to determine the current temperature and to make subsequent decisions regarding turning on, turning off, fan speed, etc. As another example, a 3D printer may communicate with a database to determine whether added devices are required to refill an inventory of available devices in a hardware store.

These and other peer-to-peer communications are regrettably susceptible to attacks emanating from a plethora of nefarious people and shadowy organizations. For example, fraudulent software applications can be inserted into the communications paths in attempts to steal industrial secrets. Another problem is that the communications can be overheard, and then used to usurp control of various pieces of equipment and cause malfunctioning thereof. As another example, viruses and other malware may be introduced into the communications system to interrupt routine communications between or among smart devices 1401, 1402, 1403. These attacks have been inhibiting the growth of the Internet Of Things and other Networks Of Things, at great cost to society.

FIG. 14 illustrates my solution to these security problems. The system comprises at least one sending smart device 1401 that has been designed to send messages 1460 over the network 1450 to one or more receiving smart devices 1402. FIG. 14 illustrates one sending smart device 1401, one receiving smart device 1402, and a plurality of additional smart devices, numbered 1403(3) through 1403(n), where n is an arbitrary integer greater than or equal to 4.

Each sending smart device 1401 is coupled to the network 1450 via a sending intelligent chip 1411. Each receiving smart device 1402 is coupled to the network 1450 via a receiving intelligent chip 1421.

Each sending intelligent chip 1411 appends a message identifier 1417 to each message 1460 emanating from its associated smart sending device 1401. The identifier 1417 comprises a fixed portion identifying the sending device type and uniquely identifying the associated sending device 1401. This unique portion is stored in memories 1415, 1416 within chip 1411. Memory 1415 stores a digitized representation of the type of the sending device 1401, and memory 1416 stores a unique digitized identification of the specific sending device 1401 associated with chip 1411. Message ID 1417 also comprises a variable portion, which, together with the fixed portion, provides realtime security without the use of encryption, PINs, or passwords.

Each receiving intelligent chip 1421 comprises a module 1423 for approving the messages 1460 being sent to the associated receiving smart device 1402. Module 1423 validates both the fixed and variable portions of the message identifier 1417.

Message 1460 contains the addresses of the one or more receiving smart devices 1402 that the sending smart device 1401 wishes to receive the message 1460. These addresses are in a format usable by the particular network 1450. For example, when network 1450 is the Internet, these addresses may be the Internet Protocol (IP) addresses of the receiving smart devices 1402. The message package that is sent by sending intelligent chip 1411 over communications link 1441 to network 1450, and then over communications link 1442 to receiving intelligent chip 1421, comprises the substantive portion of the message 1460 as originated by the sending device 1401, the address of one or more receiving smart devices 1402, and the message identifier 1417.

Communications links 1441 and 1442 can be any wired or wireless communications links.

Receiving smart device 1402, in addition to performing the functions of a receiving device, may also be built to perform the functions of a sending smart device 1401. This embodiment can be used when sending smart device 1401 desires or requires feedback to the message 1460 that it sends. In these embodiments, the sending/receiving smart device 1403 has an associated intelligent chip that has been built and programmed to perform the functions of both a sending intelligent chip 1411 and a receiving intelligent chip 1421.

In one embodiment, message ID 1417 comprises 40 digits and adheres to the ISO Track 2 format. This is a very useful embodiment, in that many industry protocols, such as magnetic stripes in debit and credit cards, and smart phones, use this format.

As illustrated in FIG. 14, sending intelligent chip 1411 comprises an optional input buffer 1412 for time buffering and/or reformatting the raw message 1460 that chip 1411 receives from sending device 1401. Message 1460 is then routed to processor 1413, which can be a conventional microprocessor. Processor 1413 typically receives inputs from three sources within chip 1411: clock 1414, which tracks the current date and time; memory 1415, which stores the type of sending smart device 1401 associated with chip 1411; and memory 1416, which stores a unique identification of the associated sending device 1401. Memories 1415 and 1416 can be populated by a human user associated with the system, or populated from initialization signals received automatically from sending device 1401.

The current date and time, as output by clock 1414, is used by processor 1413 as the variable portion of the message identifier 1417. The fixed portion of message identifier 1417 is a composite of the digitized version of the sending device type from memory 1415, and the sending device unique identifier from memory 1416. The combined variable and fixed portions of message ID 1417 are combined with the actual message 1460 (including addresses), and sent to a transmitter 1418 within chip 1411, where the message package is put in a suitable form for transmission over link 1441. Transmitter 1418 may comprise a modem, codec, or other device that is specifically tailored for that particular network 1450 and its communications protocols.

When digitizing the time received from clock 1414, processor 1413 assigns the exact current time into a digitized interval bucket. The time interval can be preselected by the user of chip 1411.

Receiving intelligent chip 1421 receives the message package via a receiver 1428 within chip 1421. Receiver 1428 is selected to be compatible with the communications protocols of network 1450 and the associated timing and formatting requirements of chip 1421, as would be well known to one of ordinary skill in the art.

The message package is then routed to processor 1423 within chip 1421 for purposes of verifying that the message 1460 is legitimate and thus appropriate to be sent on to receiving smart device(s) 1402.

The verification process performed by processor 1423 comprises a verification of the variable portion of message identifier 1417, and an independent verification of the fixed portion of message identifier 1417.

The verification of the variable portion of identifier 1417 comprises processor 1423 obtaining the current date and time from clock 1424 within chip 1421. Processor 1423 then determines whether this current time is within a preselected acceptable time period from the time that was appended by chip 1411 as part of identifier 1417. This preselected acceptable time period can be set in chip 1421 by a user of the system. This check of the current time guards against replay attacks, i.e., when a nefarious entity intercepts the message 1460, perhaps altering the message, then resends it at a later time to an unsuspecting receiving smart device 1402.

The verification of the fixed portion of identifier 1417 typically comprises processor 1423 consulting two whitelists within chip 1421. The first whitelist 1425 is a list of acceptable types of sending devices 1401. The second whitelist 1426 is a list of acceptable unique identifications of specific sending devices 1401. In an alternate embodiment, the two whitelists 1425, 1426 can be combined into a single whitelist.

When and only when both the variable and the fixed verification steps are successfully completed, processor 1423 sends the message 1460 to the one or more receiving smart devices 1402 that have been designated to receive message 1460. Message identifier 1417 may optionally be appended to message 1460 by processor 1423, to give each receiving smart device 1402 an indication of when the message 1460 was packaged by chip 1411, as well as the type and unique identification of the particular sending device 1401 that originated the message 1460.

The message 1460 is sent by chip 1421 to smart device 1402 via optional output buffer 1422, which is used when it is desired or required to put the format and/or the timing of the message 1460 into compatibility with the protocols used by receiving smart device 1402.

When processor 1423 is not able to verify the bona fides of message 1460, processor 1423 typically destroys the message 1460, because such an unverified message 1460 may cause damage to system resources if it is not eliminated.

In certain embodiments, when receiving device 1402 receives a valid message 1460, receiving device 1402 sends an acknowledgement message back to sending device 1401 through chip 1421, network 1450, and chip 1411.

In certain embodiments, all the clocks 1414, 1424 are synchronized periodically, e.g., daily, to maintain integrity of the time checks described above.

Those skilled in the art will readily recognize, in light of and in accordance with the teachings of the present invention, that any of the foregoing steps and/or system modules may be suitably replaced, reordered, and/or removed, and additional steps and/or system modules may be inserted, depending upon the needs of the particular application. The systems of the foregoing embodiments may be implemented using any of a wide variety of suitable processes and system modules, and are not limited to any particular computer hardware, software, middleware, firmware, microcode, or the like. For any method steps described in the present application that can be carried out on a computing machine, a typical computer system can, when appropriately configured or designed, serve as a computer system in which those aspects of the invention may be embodied.

It will be further apparent to those skilled in the art that at least a portion of the novel method steps and/or system components of the present invention may be practiced and/or located in location(s) possibly outside the jurisdiction of the United States of America.

All the features disclosed in this specification, including any accompanying abstract and drawings, may be replaced by alternative features serving the same, equivalent, or similar purpose, unless expressly stated otherwise. Thus, unless expressly stated otherwise, each feature disclosed is only one example of a generic series of equivalent or similar features.

Having fully described at least one embodiment of the present invention, other equivalent or alternative methods of remote authorization according to the present invention will be apparent to those skilled in the art. The invention has been described above by way of illustration, and the specific embodiments disclosed are not intended to limit the invention to the particular forms disclosed. For example, the particular implementation of Smart Device 102 may vary depending upon the particular type of computing device used. The computing devices described in the foregoing were primarily directed to smartphone device implementations; however, similar techniques using laptop computing devices are contemplated as within the scope of the present invention. The invention is thus intended to cover all modifications, equivalents, and alternatives falling within the spirit and scope of the following claims.

The invention claimed is:

1. A system wherein two or more devices communicate with each other over a network automatically and without human intervention, said system comprising:
   at least one smart sending device adapted to send substantive original messages pertaining exclusively to said smart sending device, said messages being sent over the network to at least one smart receiving device, each smart sending device coupled to the network via an associated dedicated sending intelligent chip; and
   at least one smart receiving device coupled to the network via an associated dedicated receiving intelligent chip; wherein
   each sending intelligent chip appends an identifier to each message emanating from the smart sending device associated with said sending intelligent chip, said identifier comprising a fixed portion uniquely identifying the associated smart sending device, and a variable portion;
   each sending intelligent chip comprises a clock for tracking the current date and time;
   each sending intelligent chip digitizes the time tracking by the clock according to a time interval preselected by a user of the sending intelligent chip, and makes the digitized time the variable portion of the identifier;
   each sending intelligent chip makes the type of the smart sending device and a unique identification of the smart sending device the fixed portion of the identifier; and
   each receiving intelligent chip comprises a module for approving the messages by validating both the fixed and variable portions of the identifier.

2. The system of claim 1 wherein the network is the Internet.

3. The system of claim 1 wherein the message contains the addresses of several smart receiving devices that are to be recipients of the message.

4. The system of claim 1 wherein each message comprises a substantive portion and a portion containing the address of a receiving device that the smart sending device associated with said message has designated to be a recipient of the message.

5. The system of claim 1 wherein at least one smart receiving device is reversible in that said smart receiving device is adapted to perform the functions of the aforesaid smart sending device.

6. The system of claim 5 wherein each smart device that is reversible has associated therewith an intelligent chip adapted to perform the functions of both a receiving intelligent chip and a sending intelligent chip.

7. The system of claim 1 wherein the identifier comprises 40 digits, and uses an ISO Track 2 format.

8. The system of claim 1 wherein each sending intelligent chip comprises:
   a processor;
   coupled to the processor, the clock for tracking the date and time;
   coupled to the processor, a first memory storing the type of smart sending device associated with the sending intelligent chip; and
   coupled to the processor, a second memory storing the unique identification of the smart sending device associated with the sending intelligent chip.

9. A system for enabling two or more devices to communicate with each other over a network without human intervention, said system comprising:
   least one sending device adapted to send messages over the network to at least one receiving device, each sending device coupled to the network via a sending intelligent chip; and
   at least one receiving device coupled to the network via a receiving intelligent chip; wherein:
   each sending intelligent chip appends an identifier to each message emanating from the sending device associated with said sending intelligent chip, said identifier comprising a fixed portion uniquely identifying the associated sending device, and a variable portion;
   each receiving intelligent chip comprises a module for approving the messages by validating both the fixed and variable portions of the identifier;
   each sending intelligent chip comprises:
      a processor;
      coupled to the processor, a clock for tracking the date and time;
      coupled to the processor, a first memory storing the type of sending device associated with the sending intelligent chip; and
      coupled to the processor, a second memory storing a unique identification of the sending device associated with the sending intelligent chip; and
   the sending intelligent chip processor is adapted to:
      digitize the time tracked by the dock according to a time interval preselected by a user of the sending intelligent chip, and make the digitized time the variable portion of the identifier; and
      make the type of sending device and the unique identification of the sending device the fixed portion of the identifier.

10. The system of claim 9 wherein a processor within the receiving intelligent chip approves the message from the sending device only when:
   the time portion of the identifier is within a preselected acceptable time prior to the current time;
   the type of sending device is found in a first whitelist of acceptable sending device types; and
   the unique identification of the sending device is found within a second whitelist of acceptable sending device identifications; wherein:
   said first and second whitelists are stored on the receiving intelligent chip.

* * * * *